United States Patent [19]
Bernstein et al.

[11] Patent Number: 5,721,222
[45] Date of Patent: Feb. 24, 1998

[54] HETEROCYCLIC KETONES

[75] Inventors: Peter Robert Bernstein, Wallingford; Andrew Shaw, Kennett Square, both of Pa.; Royston Martin Thomas, Macclesfield, United Kingdom; Chris Allan Veale, Newark, Del.; Peter Warner, Macclesfield, United Kingdom; Donald John Wolanin, Orange, Conn.

[73] Assignee: ZENECA Limited, London, England

[21] Appl. No.: 519,651

[22] Filed: Aug. 25, 1995

Related U.S. Application Data

[62] Division of Ser. No. 45,496, Apr. 8, 1993, Pat. No. 5,486,529.

[30] Foreign Application Priority Data

Apr. 16, 1992 [GB] United Kingdom ............ 9208385.6
Aug. 14, 1992 [GB] United Kingdom ............ 9217365.7

[51] Int. Cl.$^6$ ............ C07D 211/84; C07D 213/81; C07D 401/12; A61K 31/44
[52] U.S. Cl. ............ 514/89; 514/335; 514/346; 514/5; 514/22; 514/261; 514/291; 514/292
[58] Field of Search ............ 546/261, 291, 546/292, 22.5; 514/335, 346, 89

[56] References Cited

U.S. PATENT DOCUMENTS 4,880,870 11/1989 Trainor et al. ............ 514/18
4,910,190 3/1990 Bergson et al. ............ 514/19

FOREIGN PATENT DOCUMENTS

EP 0 195 212 A2 9/1986 European Pat. Off. .
EP 0 249 349 12/1987 European Pat. Off. .
EP 0397 427 11/1990 European Pat. Off. .
EP 0 509 769 A2 10/1992 European Pat. Off. .
EP 528 633 A1 2/1993 European Pat. Off. .

*Primary Examiner*—Alan L. Rotman
*Attorney, Agent, or Firm*—Liza D. Hohenschutz

[57] ABSTRACT

The present invention relates to certain novel heterocyclic ketones which are 1-pyridylacetamide ketones of formula I, set out herein, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these heterocyclic ketones, processes for preparing the heterocyclic ketones, pharmaceutical compositions containing such heterocyclic ketones and methods for their use.

10 Claims, No Drawings

HETEROCYCLIC KETONES

This application is a division of our prior applications Ser. No. 08/045,496, filed Apr. 8, 1993, now U.S. Pat. No. 5,486,529.

The present invention relates to certain heterocyclic ketones, in particular, certain 1-pyridylacetamide compounds, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these heterocyclic ketones, processes for preparing the heterocyclic ketones, pharmaceutical compositions containing such heterocyclic ketones and methods for their use.

In U.S. Pat. No. 4,880,780, of 14 Nov. 1989, and U.S. Pat. No. 4,910,190, of 20 Mar. 1990, assigned to ICI Americas Inc. (now ZENECA Inc.), there are disclosed two series of peptidic fluoroalkyl ketone derivatives which are HLE inhibitors. Disclosed herein is a series of substituted 2-(2-oxo-1,2-dihydro-1-pyridyl)-N-[3,3-difluoro-1-(lower alkyl)-2-oxo-3-(N-substituted carbamoyl)propyl]acetamide derivatives, which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^o$ is (1–5C)alkyl;

R is hydrogen; or

R is an acyl group of formula A.X.CO— in which A.X—, taken together, is hydrogen, trifluoromethyl, 2,2,2-trifluoroethoxy, amino, methoxyamino, 2,2,2-trifluoroethylamino, RbRcN.O—, RaOCONH—, $R^1SO_2NH$—, RaOCO—, RbRcNCO— or RaCO—; or R is an acyl group of formula A.X.CJ— in which J is oxygen or sulfur;

X is a direct bond, imino, oxy or thio; and

A is as defined below or

A is tetrahydropyran-4-yl, 1-methylpiperid-4-yl, or 5-methyl-1,3-dioxacyclohex-5-ylmethyl; or R is a sulfonyl group of formula $D.W.SO_2$— in which D.W—, taken together, is hydroxy, amino, di(lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is a group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, $CH_2COORa$, CONRbRc, $CH_2CONRbRc$, $COO(CH_2)_2NReRf$, cyano, $SO_2R^1$, $CONRdSO_2R^1$, NReRf, NRgCHO, $NRgCOR^2$, $NRgCOOR^2$, NRhCONRiRj, $NRkSO_2R^3$, $SO_2NRlRm$, $SO_2NRnCOR^4$ and $P(O)(ORa)_2$ in which Q is oxygen or sulfur;

Ra—Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl;

Each of $R^5$ and $R^6$ is, independently, hydrogen or lower alkyl; or

One of $R^5$ and $R^6$ is hydrogen or methyl and the other of $R^5$ and $R^6$ is a radical of formula B.Y— in which B is aryl or heteroaryl, which aryl or heteroaryl independently may bear one or more of the substituents defined for A, D or G or an aryl or heteroaryl moiety thereof;

Y is a direct bond, methylene, ethylene or trans-vinylene;

$R^4$ is hydrogen, (1–6C)alkyl, (3–6C)cycloalkyl, (3–6C)cycloakyl(1–3C)alkyl, aryl(1–3C)alkyl, or heteroaryl (1–3C)alkyl, wherein an aryl or heteroaryl may bear one or more halogeno, methyl or trifluoromethyl group and further wherein the group $R^4$ may bear one or more substituents selected from a group consisting of hydroxy, lower alkoxy, COORs, CONRtRu, $SO_2Rv$, $CONHSO_2Rv$, NRtRu, NRsCHO, NRsCORv, NRsCOORv, NRsCONRtRu, $NRsSO_2Rv$, $SO_2NRtRu$, $SO_2NRsCORv$, and $P(O)(ORv)_2$ in which Rs—Ru are independently hydrogen, benzyl or lower alkyl, or, independently, a group NRtRu is a cyclic radical selected from a group consisting of 1-pyrrolidinyl, piperidino, morpholino or 1-piperazinyl which may bear a lower alkyl group at the 4-position; and Rv is trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote both straight and branched groups; but reference to an individual radical such "propyl" embraces only the straight chain ("normal") radical, a branched chain isomer such as "isopropyl" being specifically referred to. Lower alkyl and lower alkoxy refer to radicals containing one to about four carbon atoms. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^O$ is isopropyl, a compound of formula I may be viewed as a valyl derivative. In general, a compound of formula I having the (S)-configuration at the chiral center indicated by "*", which corresponds to the L-alanyl configuration, is preferred. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the facile epimerization of the chiral center indicated by "*" in formula I, it may be preferred to utilize a compound of formula I as a mixture of the (S)- and (R)-isomers at the center indicated by "*" in formula I.

As will be appreciated by those skilled in the art, a ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

It is preferred that the radicals $R^4$, $R^O$, R, $R^5$ and $R^6$ not contain nor introduce an additional element of chirality into the molecule beyond the chiral center indicated by "*" in formula I.

Particular values are listed below for radicals, substituents and ranges for illustration only and they do not exclude other defined values or other values within defined ranges for the radicals and substituents.

A particular value for $R^O$ is ethyl or isopropyl.

A particular value for W is a direct bond or imino.

A particular value for G is (1–3C)alkyl, aryl(1-C)alkyl or heteroaryl(1–2C)alkyl which may bear one or more substituents as defined above for G or a part thereof.

A particular value of (1–6C)alkyl is methyl, ethyl, propyl, isopropyl, butyl, isobutyl, t-butyl, pentyl, 3-methylbutyl, 1-ethylpropyl, hexyl or 4-methylpentyl. A particular value of (3–6C)cycloalkyl is cyclopropyl, cyclopentyl or cyclohexyl. A particular value for the (1–3C)alkyl portion of (3–6C)cycloalkyl(1–3C)alkyl, aryl(1–3C)alkyl or heteroaryl(1–3C)alkyl is methylene, ethylene or trimethylene. A particular value for aryl is phenyl, indenyl, indanyl or naphthyl. A particular value for heteroaryl is furyl, imidazolyl, tetrazolyl, pyridyl (or its N-oxide), thienyl, pyrimidinyl (or its N-oxide), indolyl or quinolinyl (or its N-oxide). A particular value for lower alkyl is methyl, ethyl, propyl, isopropyl, butyl, isobutyl or !-butyl. A particular value for lower acyloxy is acetoxy. A particular value for lower alkoxy is methoxy, ethoxy, propoxy, isoproxy or t-butoxy. A particular value for halogeno is bromo, chloro or fluoro.

A particular value for COORa is carboxy or methoxycarbonyl. A particular value for NRgCOR² is trifluoroacetylamino. A particular value of CONRdSO₂R¹ is N-phenylsulfonylcarbamoyl or N-(4-chlorophenylsulfonyl)carbamoyl. A particular value for A.X—, taken together, is tris(hydroxymethyl)methylamino, tris(acetoxymethyl)methylamino or 2,2-bis(hydroxymethyl)propoxy.

A more particular value for $R^O$ is isopropyl. A more particular value for J is oxygen. A more particular value for X is a direct bond, imino or oxy. A more particular value for A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for D is methyl, ethyl, isopropyl, tert-butyl, cyclohexyl, phenyl, benzyl, phenethyl, pyridyl, thienyl, 5-tetrazolyl, thiazolyl, quinolinyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonamido, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for G is methyl, ethyl, benzyl, phenethyl, pyridyl, pyridylmethyl, thenyl, 5-tetrazolylmethyl, or 2-(pyridyl)

ethyl, wherein an alkyl carbon may bear an oxo group and wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

A particular value for R is, for example, hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolinylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

A particular value for $R^4$ is, for example hydrogen, methyl, ethyl, propyl,2-(3–6C)cycloalkylethyl, phenethyl, 2-(pyridyl)ethyl, (wherein the phenyl or pyridyl group may bear one or two halogeno or methyl groups and further wherein the group $R^4$ may bear a substituent selected from hydroxy, methoxy, carboxy, methoxycarbonyl, ethoxycarbonyl, carbamoyl, methylsulfonyl, N-methsulfonylcarbamoyl, N-phenylsulfonylcarbamoyl, amino, and dimethylamino) or 2-(dimethylamino)ethyl, 2-morpholinoethyl, 2-piperidinoethyl or 2-(4-methylpiperazin-1-yl)ethyl.

One particular group of compounds of formula I is one in which $R^4$, $R^O$ and R have any of the values defined above, $R^5$ is hydrogen and $R^6$ is hydrogen.

Another particular group of compounds of formula I is one in which $R^4$ $R^O$ and R have any of the values defined above, $R^5$ is benzyl, the phenyl ring of which may bear a 3-fluoro, 4-fluoro, 4-trifluoromethyl, 4-methoxycarbonyl, 3-acetoxy, 3-hydroxy, 3-pivaloyloxy, 4-hydroxy, 4-pivaloyloxy, 3-trifluoroacetylamino or 3-amino substituent, and $R^6$ is hydrogen.

A further particular group of compounds of formula I is one in which $R^4$ $R^O$ and R have any of the values defined above, $R^5$ is hydrogen, and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl, 4-fluorophenyl or 2-thienyl.

Specific compounds of formula I are described in the accompanying Examples. Of these, compounds of particular interest, along with their pharmaceutically acceptable salts, include those described in Examples 2 and 5.

A pharmaceutically acceptable salt of an acidic compound of formula I is one made with a base which affords a pharmaceutically acceptable cation, which includes alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. A pharmaceutically acceptable salt of a basic compound of formula I includes an acid-addition salt made with an acid which provides a pharmaceutically acceptable anion, including for example, a strong acid such as hydrochloric, sulfuric or phosphoric acid.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II. If R is hydrogen or a group G, it will be recognized that protection of the pyridone 3-amino substituent prior to oxidation and removal of the protecting group after oxidation may be preferred or required if the amino group is not stable to the oxidation conditions employed. A convenient method is the use of excess dimethyl sulfoxide and a water soluble carbodimide, with dichloroacetic acid as a catalyst, in a inert solvent such as toluene at about room temperature, for example as described in Example 1, part i. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)-one with trifluoroacetic acid in dichloromethane.

(B) For a compound of formula I which contains an N—H residue, removal by using a conventional method of the nitrogen protecting group of a corresponding compound bearing a conventional nitrogen protecting group to afford the compound of formula I which contains an amino N—H residue, particularly for a compound of formula I in which R is hydrogen, removal of a group from a corresponding compound of formula I, or for a compound of formula I in which R has a value of G, the removal of an activating/protecting group Rx from a corresponding compound of formula Vb. Rx is a group which protects and activates a primary amino group for substitution, such as for example benzyloxycarbonyl or trifluoroacetyl. Conventional methods include, for example, removal of a benzyloxycarbonyl group by hydrogenolysis, removal of a benzyloxycarbonyl or tert-butoxycarbonyl group by treatment with a strong acid, for example with trifluoromethanesulfonic acid in an inert solvent such as dichloromethane, or basic hydrolysis of a trifluoroacetyl group.

(C) For a compound of formula I wherein R is an acyl group, acylation of a corresponding amine of formula I wherein R is hydrogen. Convenient methods include those described below for acylation of an amine of formula IX, for example, when J is oxygen, the use of an activated carboxylic acid derivative, such as an acid halide, the use of a carboxylic acid and a coupling reagent, the use of an isocyanate for a compound wherein X is imino, and the use of a diactivated carbonic acid derivative, for example, carbonyldiimidazole, phosgene, diphosgene (trichloromethyl chloroformate) or triphosgene (bis (trichloromethyl) carbonate) with an alcohol of formula A.OH, a thiol of formula A.SH or an amine of formula $A.NH_2$ and a base, such as triethylamine or, when J is sulfur, the use of an activated thiocarboxylic acid derivative, such as a thioyl chloride or a lower alkyl ester of a dithioic acid, the use of a thioic acid and a coupling reagent, the use of an isothiocyanate for a compound wherein X is imino, and the use of a diactivated thiocarbonic acid derivative, for example, dimethyl trithiocarbonate, with an alcohol of formula A.OH, a thiol of formula A.SH or an amine of formula $A.NH_2$.

(D) For a compound of formula I wherein R is a sulfonyl group, sulfonylation of a corresponding amine of formula I wherein R is hydrogen with a corresponding sulfonic acid of formula $D.W.SO_2.OH$, or an activated derivative thereof, such as an acid halide, particularly a sulfonyl (or sulfamoyl) chloride of formula $D.W.SO_2.Cl$. The sulfonylation is conveniently carried out in an inert solvent or diluent, such as dichloromethane, tetrahydrofuran or toluene, at about ambient temperature, using an organic base such as, for example, triethylamine or pyridine, or an inorganic base, such as sodium or potassium carbonate, as an acid acceptor. If a sulfonyl chloride is not commercially available, it may be obtained by a conventional method.

(E) For a compound of formula I in which R is a group G, substitution of the group L of a corresponding compound of formula G—L, wherein L is a conventional leaving group, such as for example halogeno, methylsulfonyloxy, trifluoromethylsulfonyloxy or diazonium, with a corresponding amine of formula I wherein R is hydrogen, optionally using a conventional catalyst.

(F) For a compound of formula I which bears a hydroxy substituent on an aryl or heteroaryl group, cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide or pyridinium chloride and the cleavage of a t-butoxy group using trifluoroacetic acid for an alkyl ether, and the acidic or alkaline hydrolysis of an acyloxy group.

(G) For a compound of formula I which bears a group of formula COORa or COORs in which Ra or Rs is hydrogen (a carboxy group), decomposing the ester group of a corresponding ester made with a conveniently removed acid protecting group, for example a corresponding compound of formula I in which Ra or Rs is not hydrogen. The decomposition may be carried out using any one of the variety of procedures well known in organic chemistry, for example basic hydrolysis using lithium or sodium hydroxide, or by hydrogenolysis of a benzyl ester.

(H) For a compound of formula I bearing a moiety of formula COORa, $CH_2COORa$, CONRbRc, $CH_2CONRbRc$, $COO(CH_2)_2NReRf$ or $CONRdSO_2R^1$, acylation of a corresponding compound of formula HORa, HNRbRc, HO$(CH2)_2NReRf$ or $HNRdSO_2R^1$ with a corresponding acid of formula I bearing a moiety of formula COORa in which Ra is hydrogen, or an activated derivative thereof; or, correspondingly, for a compound of formula I bearing a moiety of formula COORs, CONRtRu or $CONHSO_2Rv$, acylation of a corresponding compound of formula HORs, HNRtRu or $H_2NSO_2Rv$ with a corresponding acid of formula I bearing a moiety of formula COORs in which Rs is hydrogen, or an activated derivative thereof.

(I) For a compound of formula I bearing a lower acyloxy group or a group of formula NRgCHO, $NRgCOR^2$, $NRgCOOR^2$, NRhCONRiRj or $NRkSO_2R^3$ acylation or sulfonylation of a corresponding compound of formula I bearing a hydroxy group or an amino group of formula NHRg, NHRh or NHRk (i.e. an amino group of formula NReRf is which Re is hydrogen and Rf is Rg, Rh or Rk) with an activated derivative of a corresponding acid of formula HOCHO, $HOCOR^2$, $HOCOOR^2$, HOCONRiRj (including an isocyanate or isothiocyanate) or $HOSO_2R^3$, respectively, using a conventional method; or, correspondingly, for a compound of formula I bearing a group of formula NRsCORv, NRsCOORv, NRsCONRtRu or $NRsSO_2Rv$, acylation or sulfonylation of a corresponding compound of formula I bearing an amino group of formula NRtRu in which Rt has a value defined for Rs and Ru is hydrogen with an activated derivative of a corresponding acid of formula HOCORv, HOCOORv, HOCONRtRu (including an isocyanate) or $HOSO_2Rv$, respectively using a conventional method.

(J) For a compound of formula I which bears a heteroaryl N-oxide group, oxidation of a corresponding compound of formula I which bears a heteroaryl group using a conventional oxidant, such as for example dioxirane in acetone.

(K) For a compound of formula I which bears a primary amino group, reduction of a corresponding compound bearing a nitro group using a conventional reducing method, such as for example, hydrogenation over a palladium catalyst, or reduction with tin(II) chloride.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the 2-pyridone, rather than the 2-hydroxypyridine, tautomers.

As will be clear to one skilled in the art, a variety of sequences is available for preparation of the starting materials. According to one of the available routes, a key intermediate pyrid-2-one-3-carboxylic acid of formula III may be prepared as shown in Scheme I (set out, together with other Schemes, following Examples). In the Schemes, CBZ represents a benzyloxycarbonyl group.

In general, in a formal sense, a ketone of formula $R^5.CH_2.CO.R^6$ may be formylated, then cyclized with cyanoacetamide to afford a pyrid-2-one-3-carbonitrile of formula IV. Thus, (Cyclization Method A) the ketone may be formylated with dimethylformamide dimethyl acetal in acetonitrile, then the isolated intermediate cyclized with cyanoacetamide, using sodium methoxide in dimethylformamide. Alternatively, (Cyclization Method B) the ketone may be formylated using sodium methoxide and ethyl formate in tetrahydrofuran or ether, distilling the solvent, dissolving the resulting salt in water, adding acetic acid to pH 9, and heating with cyanoacetamide at 90° C. to achieve the cyclization. As a further variation, (Cyclization Method C) the salt resulting from formylation with sodium methoxide and ethyl formate, followed by removal of the solvent, may be cyclized with cyanoacetamide by heating an aqueous solution with piperidine acetate as a catalyst. Where more than one product is possible from the cyclization reaction, the product selectivity may be controlled by the cyclization (and formylation) method chosen. For example, cyclization of phenylacetone by Cyclization Method A affords 6-methyl-5-phenyl-pyrid-2-one-3-carbonitrile; but cyclization of phenylacetone by Cyclization Method C affords 6-benzylpyrid-2-one-3-carbonitrile. Hydrolysis of the cyano group of a compound of formula IV, for example by heating with 48% hydrobromic acid in acetic acid (Hydrolysis Method A) or with sodium hydroxide solution in a pressure vessel (Hydrolysis Method B) affords a corresponding carboxy derivative of formula III. For a compound in which $R^6$ is B.Y— and Y is ethylene or trans-vinylene, it may be preferred to proceed via an alternative route to an acid of formula III. Thus, cyclization of a ketone of formula $R^5.CH_2.CO.CH_3$ affords a 6-methyl pyridone derivative of formula IVa, for example, cyclizing acetone by Cyclization Method C. Bis-metallation, followed by alkylation with a reagent of, for example, formula $B.CH_2.Br$ affords a corresponding nitrile of formula IV in which Y is ethylene. Alternatively, bis-metallation of a 6-methyl pyridone of formula IVa, followed by condensation with an aldehyde of formula B.CHO, affords a pyrid-2-one-3-carbonitrile of formula IVb which may be converted by acid hydrolysis and dehydration into a corresponding pyride-2-one-3-carboxylic acid of formula III in which Y is trans-vinylene.

An acid of formula III may be converted into a corresponding isocyanate of formula VI by a conventional method, for example by using triethylamine and diphenylphosphoryl azide in an inert solvent, for example dioxane or toluene, at an elevated temperature. Conveniently, the isocyanate is not isolated, but is converted into a benzyl urethane of formula VII as also is shown in Scheme I. It will be clear to one skilled in the art that, in general, treatment of an isocyanate of formula VI with a selected alcohol or amine of formula A.X.H. in which X is oxy or imino will provide a corresponding product of formula VIIa in which X is oxy or imino, and that the product of formula VIIa may be carried forward to an alcohol of formula II using one of the routes outlined below. (An isocyanate of formula VI may undergo intramolecular cyclization to the oxygen at the pyridone 2-position, thereby forming a corresponding cyclic carbamate, which carbamate similarly may afford a corresponding compound of formula VII or VIIa.)

Elaboration of a substituted amino pyridone of formula VII or VIIa into a corresponding intermediate alcohol of formula II or a corresponding intermediate amine of formula Vb may be carried out as outlined. Thus, a pyridone of formula VII may be alkylated, for example with ethyl or t-butyl iodoacetate using sodium hydride in dimethylformamide, to afford a corresponding ester of formula XI, wherein Rq is a conveniently removable acid protecting group, for example ethyl or t-butyl. (The corresponding 2-alkoxypyridine resulting from O-alkylation is also obtained. When $R^6$ is subject to hindered rotation, for example when $R^5$ is methyl and $R^6$ is phenyl, or, for example, when $R^5$ is hydrogen and $R^6$ is 2-chlorophenyl, the ratio of N-alkylated product to O-alkylated product is increased.) Removal of the acid protecting group of an ester of formula XI by a conventional method, for example by base catalyzed hydrolysis or by acid catalyzed elimination, affords a corresponding acid of formula XII.

An alternative route for the preparation of an intermediate acid of formula XII, beginning with a ketone of formula $R^5.CH_2.CO.R^6$ and involving a novel pyridone synthesis, which may be a preferred route, is described in Example 1, parts a.-f., for the conversion of acetophenone into 3-benzyloxycarbonylamino-2-oxo-6-phenyl-1,2-dihydro-1-pyridylacetic acid.

The intermediate amines of formulae A, B and C, may be prepared as outlined in Scheme Ia using known or analogous methodology. For example, the preparation of the common intermediate of formula D wherein $R^o$ is isopropyl from L-valinol described in Example 1 of U.S. Pat. No. 4,880,780, as is the corresponding compound of formula E in which $R^A$ is benzyl. Preparations of the intermediate of formula D wherein $R^o$ is isopropyl and corresponding intermediates of formulae E and B (for example with $R^A$ as propyl or phenethyl) are also described in European Patent Application, Publication No. 397,427 A1, inter alia. The hydroxy group of a compound of formula E may be protected by a conventional method to afford a corresponding compound of formula F, wherein Rp represents an alcohol protecting group, conveniently tert-butyldimethylsilyl. Removal of the amine protecting group of a compound of formula D, E or E by a conventional method, for example as described in Example 1 under part g, affords a corresponding amine of formula A, B or C, which may be conveniently isolated and used as its acid addition salt, for example the hydrochloride or hydrobromide salt. As outlined in Scheme II, an acid of formula XII may be coupled with an amine of formula A, B or C, for example as described in Example 1, part g, to afford a corresponding product of formula VIIIc, VIIIa or VIII, respectively. Treatment of an ester of formula VIIIc with an amine of formula $R^A NH_2$, for example as described in Example 1, part h, affords a corresponding amine of formula VIIIa. By using a conventional method, for example as described in Example 2, part a, the hydroxy group of a compound of formula VIIIa may be protected to afford a corresponding compound of formula VIII. (Conversely, a compound of formula VIII may be deprotected to afford a compound of formula VIIIa.)

The benzyloxycarbonyl group of a compound of formula VIII may be removed by a conventional method, for example by hydrogenolysis as described in Example 2, part b, to afford a corresponding 3-amino pyridone of formula IX. A 3-amino pyridone of formula IX may then be acylated, sulfonylated or be substituted with a group G by using a conventional method to afford a corresponding pyridone of formula X. Conventional acylation and sulfonylation methods and methods for introducing a group G include those described above in processes (C), (D) and (E) for substituting an amine of formula I wherein R is hydrogen. (Should a portion of bis-sulfonylated product be obtained, treatment with aqueous base at an elevated temperature may be used to remove the more labile second sulfonyl group at a convenient stage in the synthesis.) Removal of a tert-butyldimethylsilyl group to provide a corresponding alcohol of formula II may be carried out using tetrabutylammonium fluoride in an inert solvent, for example as described in Example 2, part d; it may be preferred to use acetic acid to buffer the reaction conditions. An alternative order of steps can be used as well. Thus, removal of the alcohol protecting group of a compound of formula VIII affords the corresponding alcohol of formula VIIIa. Deprotection of the amino group of a compound of formula VIIIa affords a corresponding amino ketone of formula XXVII (see Scheme IV for formula XXVII) which may be converted into a corresponding compound of formula II using a conventional procedure as described above for conversion of a compound of formula IX into a compound of formula X.

Alternatively, oxidation of an alcohol of formula VIIIa (which is a compound of formula II wherein R is benzyloxycarbonyl), using a method similar to one described in process (A) for oxidation of an alcohol of formula II, affords a corresponding ketone of formula I wherein R is benzyloxycarbonyl. Removal of the nitrogen protecting group of a ketone of formula I wherein R is benzyloxycarbonyl by hydrogenolysis or by treatment with a strong acid, for example as described in Example 1, affords a corresponding amine of formula I wherein R is hydrogen.

A preferred method for introducing the substituent R when it is a group G, particularly when it is an alkyl or substituted alkyl group, is by the use of a corresponding compound in which the pyridone 3-amino substituent bears an activating/protecting group of formula Rx, for example, benzyloxycarbonyl or trifluoroacetyl. Thus, acylation of a compound of formula I wherein R is hydrogen with trifluoroacetic anhydride affords a corresponding compound of formula Va in which Rx is trifluoroacetyl, which compound also may be prepared by an alternative order of steps via the corresponding compound of formula IX. It will be noted that a compound of formula VIIIb is, itself, a corresponding compound of formula Va in which Rx is benzyloxycarbonyl. Also, each of a compound of formula Va in which Rx is benzyloxycarbonyl or trifluoroacetyl is also a compound of formula I in which R is an acyl group. Alkylation, using a corresponding reagent of formula G.L in which G is alkyl or substituted alkyl, then provides a corresponding intermediate of formula Vb.

Synthesis routes involving a cross coupling reaction to introduce a substituent $R^5$ into intermediate compounds are outlined in Scheme III. These routes may be preferred when $R^5$ has the value B.Y— and Y is methylene, ethylene or trans-vinylene. Thus, a pyridone of formula VII in which $R^5$ is hydrogen may be converted into a corresponding 5-iodo pyridone of formula XXI by treatment with an iodinating agent, for example N-iodosuccinimide. An appropriate halide, for example a bromide of formula $B.CH_2.Br$, may be converted into a corresponding organozinc reagent, for example $B.CH_2.Zn.Br$, by treatment with zinc dust in tetrahydrofuran, and cross-coupled with an iodide of formula XXI using a palladium catalyst, such as dichloro[1,1'-bis(diphenylphosphino)ferrocene]palladium(II) to afford a corresponding compound of formula VII in which $R^5$ is B.Y— and Y is methylene. A similar cross coupling utilizing a bromide of formula B.Y.Br in which Y is trans-vinylene may be useful to convert an iodide of formula XXI into a corresponding compound of formula VII in which $R^5$ is B.Y— and Y is trans-vinylene. At a convenient point in a synthesis, a compound in which $R^5$ is B.Y— and Y is trans-vinylene may be hydrogenated to afford a corresponding compound in which $R^5$ is B.Y— and Y is ethylene.

Alternatively, using a method described above, an iodide of formula XXI may be converted into a corresponding iodide of formula XXII or XXIII which may be further cross coupled as described above to provide a corresponding compound of formula VIII or XI.

Alternative synthesis routes in which a 3-nitro pyridone serves as a precursor to a 3-amino pyridone are outlined in Scheme IV. They may be particularly useful when the 3-nitro derivative is readily available, such as when $R^5$ and $R^6$ are hydrogen. Alternatively, beginning with a ketone of formula $R^5.CH_2.CO.R^6$ the corresponding 3-nitropyridone may be prepared in a manner analogous to Cyclization Method A by heating a dimethylformamide solution of the ammonium salt of nitroacetamide (prepared according to *J. Org. Chem.* (1958), 23, 113–114) with the product isolated from treatment of the ketone with dimethylformamide dimethyl acetal in acetonitrile. Direct reduction of the nitro group, followed by substitution (particularly acylation or sulfonylation) of the amine obtained, provides a pyridone of formula VIIb, which may be converted into a corresponding intermediate of formula II or formula Vb using a route similar to one outlined above for a compound of formula VII. Using a different order of steps, the 3-nitro pyridone may be alkylated first to provide an ester of formula XXIV. The ester of formula XXIV may be converted into the corresponding acid of formula XXV. The acid of formula XXV also may be obtained by allylation of the starting 3-nitro pyridone, followed by oxidative cleavage of the 1-allyl group using potassium permanganate. By coupling with the appropriate amino alcohol, an acid of formula XXV may be converted into a nitro alcohol of formula XXVI. A nitro alcohol of formula XXVI may be reduced to afford a corresponding 3-amino pyridone of formula XXVII. Substitution of a 3-amino pyridone of formula XXVII using a similar procedure to one described above affords a corresponding intermediate alcohol of formula II. In addition, a nitro alcohol of formula XXVI may be oxidized to a corresponding nitro ketone of formula XXVIII. Reduction of the nitro group of a nitro ketone of formula XXVIII affords an intermediate amine of formula I in which R is hydrogen. An analogous route from a nitro compound of formula XXIV involves first reducing the nitro group to afford a corresponding amino compound of formula XXIX. Substitution of the amino group of a compound of formula XXIX using a method similar to one described above affords a compound of formula XIb, which may be further converted into a corresponding compound of formula II or formula Vb using a similar method to one described above for a compound of formula XI, that is, conversion into a corresponding acid of formula XIIb, followed by coupling with a requisite amino alcohol.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

Inhibition Measurements

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. In general, the $K_i$ values for Compounds of the invention which were tested are generally on the order of $10^{-7}M$ or much less.

Acute Lung Injury Model

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model (described in Williams, et al., *American Review of Respiratory Diseases* (1991), 144, 875–883) was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 µg), or by dosing them intravenously or orally as solutions at various times prior to the HLE challenge (100 µg) to determine their utility preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

Acute Hemorrhagic Assay

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respirator Disease* (1990), 141, 672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 µg/animal of HNE in 300 µL phosphate buffered saline (PBS) pH 7.4. Four hours after enzyme administration, the animals are killed with an overdose of phenobarbital sodium, the thorax opened and the lungs and trachea removed. The excised lungs are lavaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (µL blood equivalents)/(mL lavage) are determined by comparing the OD of the test samples with the OD of the standard curve prepared from whole hamster blood. The total µL equivalents of blood recovered is determined by multiplying recovered lavage volume by the (µL blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that, as would be expected in comparison of in vitro and in vivo results, there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorrhagic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In a liquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No.

3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, an 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of an HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route, either alone or simultaneously or sequentially with other therapeutically active agents customarily administered for the condition.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); if "acidic silica gel" is indicated, material custom prepared by J. T. Baker Chemical Co., Phillipsburg, N.J., USA, and having a pH of about 6 when slurried in water was used; reversed phase chromatography means flash chromatography over octadecylsilane (ODS) coated support having a particle diameter of 32–74 μ, know as "PREP-40-ODS" (Art 731740-100 from Bodman Chemicals, Aston, Pa., USA); thin layer chromatography (TLC) was carried out on 0.25 mm silica gel GBLF plates (Art 21521 from Analtech, Newark, Del., USA); reversed phase-TLC (RP-TLC) was carried out What-man $MKC_{18}F$ plates (Art 4803-110 from Bodman Chemicals);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-$d_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported.

EXAMPLE 1

2-(3-Amino-2-oxo-6-phenyl-1,2-dihydro-1-pyridyl)-N-[3,3-difluoro-1-isopropyl-2-oxo-3-(N-phenethylcarbamoyl)propyl]acetamide To a solution of 2-(3-benzyloxycarbonylamino-2-oxo-6-phenyl-1,2-dihydro-1-pyridyl)-N-[3,3-difluoro-1-isopropyl-2-oxo-3-(N-phenethylcarbamoyl)propyl]acetamide (0.451 g) in dichloromethane (7 mL) and anisole (0.22 mL) was added trifluoromethanesulfonic acid (0.30 mL). After 1.5 h, the reaction was quenched with saturated sodium bicarbonate. The mixture was extracted with dichloromethane, and the extracts were washed (saturated sodium bicarbonate, brine), dried, and evaporated. The crude product was purified by chromatography, twice, with dichloromethane:methanol (first column: gradient, 99:1, 92:8; second column: gradient, 99:1, 92:8) as the eluent. The resulting material was crystallized from ether and petroleum ether to give the title compound (0.119 g) as a tan solid; TLC: $R_f$=0.27, dichloromethane:methanol (98:2); 300 MHz NMR: 9.20 (t,1), 8.42 (d,1), 7.38–7.18 (m,10), 6.51 (d,1), 5.97 (d,1), 5.15 (d,2), 4.80 (dd,1), 4.43 (broad s,2), 3.43–3.29 (m,2), 2.76 (t,2), 2.29–2.13 (m,1), 0.85 (d,3), 0.74 (d,3); MS: m/z=525(M+1).

Analysis for $C_{28}H_{30}F_2N_4O_4$: Calculated: C, 64.11; H, 5.76; N, 10.68; Found: C, 64.26; H, 5.90; N, 10.52.

a. 3-Aza-4-phenylpent-3-enal dimethyl acetal

Acetophenone (60.6 g) and aminoacetaldehyde dimethyl acetal (78.9 g) were dissolved in toluene (650 mL) in a 1 L round-bottomed flask. A Dean-Stark trap, fitted with a reflux condenser, was attached to the reaction vessel and the solution was brought to reflux. The trap was drained after 17, 41, and 48 hours (30 mL each time). After 65 hours, the reaction was cooled and volatiles were evaporated to leave a yellow liquid (103.3 g). Fractional distillation gave two major fractions: fraction 1, 10.5 g (60°–126° C., 20–24 Pa); fraction 2, 78.66 g (126°–130° C., 17–20 Pa). Fraction 1 contained a significant amount of acetophenone and amino acetaldehyde dimethyl acetal. Fraction 2 contained less than 5% acetophenone and acetal, and was used directly in the next step. The NMR spectrum was obtained from a clean fraction of imine produced in a different run; 300 MHz NMR: 2.20 (s,3), 3.33 (s,6), 3.54 (d,2), 4.70 (t,1), 7.38–7.43 (m,3), 7.79–7.82 (m,2).

b. Dimethyl 4-aza-6,6-dimethoxy-3-phenylhex-2-enylidinemalonate

A dry, 2 L, 3-necked flask was equipped with a mechanical stirrer, an addition funnel and a Claisen adapter fitted with a thermometer and a nitrogen inlet. To the reaction vessel was added a solution of lithium diisopropylamide (230 mL, 2.0M in hexane/tetrahydrofuran) and tetrahydrofuran (700 mL). To the cooled (5° C.) solution was added the crude material from Example 1.a. (78.5 g) in tetrahydrofuran (150 mL) over 30 minutes. The internal temperature was maintained at 5° C. during the addition and for 45 minutes thereafter. A solution of dimethyl methoxymethylenemalonate (70.5 g) in dry tetrahydrofuran (150 mL) was added dropwise over 30 min. The dark amber reaction mixture was allowed to warm to room temperature and was stirred overnight. The mixture was diluted with dichloromethane (2 L) and washed (saturated ammonium chloride). The aqueous washes were back extracted with dichloromethane. The combined dichloromethane layers were washed (brine) and dried ($MgSO_4$). Evaporation gave the crude diene ester (147.6 g) as a red oil. This material was used without further purification. A separate iteration of this procedure provided a clean sample for characterization after chromatography; chromatography solvent: ethyl acetate:chloroform (5:95); TLC: $R_f$=0.32, ethyl acetate:chloroform:methanol (5:95:1); 300 MHz NMR: 3.33 (s,6), 3.48 (s,3), 3.68 (s,3), 4.63 (broad s,1), 6.17 (d,1), 7.33–7.35 (m,3), 7.52–7.54 (m,3), 7.90 (broad s,1); MS: m/z=350(M+1).

c. 1-(2,2-Dimethoxyethyl)-6-phenylpyrid-2-one-3-carboxylic acid

A 3 L round-bottomed flask was equipped with a stir bar and fitted with a Claisen adapter holding a thermometer and a nitrogen inlet. The flask was charged with a solution of the product from Example 1.b. in methanol (1.5 L). Sodium methoxide (32.4 g) was added in one portion and caused a mild warming. After 3 hours, aqueous sodium hydroxide (750 mL, 10% w/v) was added to the mixture in one portion. The mixture was stirred at room temperature for 2 hours, the methanol was evaporated, and the aqueous residue was acidified with hydrochloric acid and extracted with dichloromethane. The extracts were washed (brine), dried ($MgSO_4$), and evaporated to give a red-brown oil (99.6 g) which partially solidified. This material was used without further purification. A sample of the pyridone, after purification, was characterized; TLC: $R_f$=0.41, methanol:chloroform:acetic acid (1.5:98:0.5); 300 MHz NMR: 3.13 (s,6), 4.14 (d,2), 4.63 (t,1), 6.64 (d,1), 7.51–7.58 (m,5), 8.41 (d,1).

d. 3-Benzyloxycarbonylamino-2-oxo-6-phenyl-1,2-dihydro-1-pyridylacetaldehyde dimethyl acetal An oven-dried, 3 L, three-necked flask was equipped with a mechanical stirrer, a thermometer and a reflux condenser capped with a nitrogen inlet. The reaction vessel was charged with a dioxane (1 L) solution of the product from Example 1.c. (99.6 g). Diphenylphosphoryl azide (103.9 g) and triethylamine (39.8 g) were each added to the reaction vessel in one portion and washed down with dioxane (50 mL each). The resulting solution was heated at gentle reflux (100° C.) for 1 hour. Gas evolution was vigorous at first but then subsided. The reaction mixture was cooled to 70° C., and benzyl alcohol (38.9 g) was added in one portion along with a dioxane wash (100 mL). The reaction was heated at reflux for 18 hours, cooled and evaporated. The residual oil was dissolved in ethyl acetate (1 L) and washed with 1N hydrochloric acid:brine (1:1), followed by brine. The organic layer was dried ($MgSO_4$) and evaporated to give the crude mixture (249.5 g). This material was purified by chromatography, with ethyl acetate:dichloromethane (gradient, 0:100, 5:95) as the eluent, to yield the amide (43.1 g); TLC: $R_f$=0.49, ethyl acetate:chloroform (5:95); 300 MHz NMR: 3.09 (s,6), 4.02 (d,2), 4.54 (t,1), 5.19 (s,2), 6.19 (d,1), 7.34–7.50 (m,5), 7.89 (d,1), 8.54 (s,1).

e. 3-Benzyloxycarbonylamino-2-oxo-6-phenyl-1,2-dihydro-1-pyridylacetaldehyde The product from Example 1.d. (43.1 g) was dissolved in a mixture of tetrahydrofuran (700 mL) and aqueous hydrochloric acid (225 mL 3N). The mixture was held at reflux under nitrogen for 3.5 hours. The mixture was cooled and the tetrahydrofuran was evaporated. The aqueous residue was extracted with dichloromethane, washed (saturated aqueous sodium bicarbonate) and dried ($MgSO_4$). Evaporation gave the crude product as a tan solid. Trituration with ether (300 mL) gave the aldehyde (27.3 g) as a white solid; TLC: $R_f$=0.32, ethyl acetate:dichloromethane (5:95); 300 MHz NMR: 4.66 (s,2), 5.19 (s,2), 6.28 (d,1), 7.32–7.49 (m,10), 7.94 (d,1), 8.61 (s,1), 9.50 (s,1); MS: m/z=363(M+1).

f. 3-Benzyloxycarbonylamino-2-oxo-6-phenyl-1,2-dihydro-1-pyridylacetic acid

A 2 L, three-necked flask was equipped with a mechanical stirrer, an addition funnel and a Claisen adapter holding a thermometer and a reflux condenser capped with a nitrogen inlet. The flask was charged with a tetrahydrofuran (275 mL) solution of the product from Example 1.e. (40.5 g). The addition of tert-butanol (275 mL) caused precipitation of the aldehyde starting material. The reaction mixture was cooled to 15° C. with an ice-water bath, and 2-methyl-2-butene (250 mL) was added in one portion. A solution of sodium chlorite (80%, 88.5 g) and sodium dihydrogen phosphate monohydrate (108.0 g) in water (400 mL) was added dropwise to the reaction mixture over 45 minutes. The internal temperature was maintained at 20° C. during the addition. Stirring at room temperature was continued for 2 hours. The mixture was partially evaporated to leave an aqueous suspension of white solid. The mixture was diluted with brine and extracted with chloroform. The combined extracts were dried ($MgSO_4$) and evaporated. The residue was dissolved in diethyl ether and evaporated to give an off-white solid, which was triturated with hexane:diethyl ether (9:1) to give the acid as an off-white solid (43.1 g); TLC: $R_f$=0.20, methanol:dichloromethane:acetic acid (2:97.9:0.1); 300 MHz NMR: 4.44 (s,2), 5.19 (s,2), 5.24 (d,1), 7.33–7.51 (m,10), 7.92 (d,1), 8.59 (s,1), 13.07 (broad s,1); MS: m/z=379(M+1). NMR showed that this material was pure but contained diethyl ether, which was not removed by prolonged drying in a vacuum oven.

g. 2-(3-Benzyloxycarbonylamino-2-oxo-6-phenyl-1,2-dihydro-1-pyridyl)-N-(3,3-difluoro-3-ethoxycarbonyl-2-hydroxy-1-isopropyl)-acetamide To a mixture of the product from Example 1.f. (20 g), ethyl (4S)-4-amino-2,2-difluoro-3-hydroxy-5-methylhexanoate hydrobromide (17.4 g), 1-hydroxybenzotriazole hydrate (14.6 g) and 4-methylmorpholine (14.6 mL) in tetrahydrofuran (350 mL) was added 1-(3-dimethylaminopropyl)-3-ethylcarbodiimide hydrochloride (11.2 g). After overnight stirring, the reaction mixture was diluted with ethyl acetate (1 L), washed (10% hydrochloric acid, saturated sodium bicarbonate, brine), dried, and evaporated. The crude product was divided into two batches and each was purified by chromatography. First batch; eluting with dichloromethane:ether (95:5), then dichloromethane:tetrahydrofuran (gradient, 97:3, 95:5), then dichloromethane:methanol (gradient, 98:2, 92:8); second batch: eluting with toluene:tetrahydrofuran (gradient, 99:1, 90:10, 80:20), to give the amide (22 g); TLC: $R_f$=0.30, dichloromethane:methanol (99:1); 300 MHz NMR: 8.51 (s,1), 7.90 (d,1), 7.75 (d,1), 7.50–7.32 (m,10), 6.23–6.20 (m,2), 5.19 (s,2), 4.45 (q,2), 4.36–4.17 (m,2), 4.13–4.04 (m,1), 3.81 (t,1), 1.79–1.68 (m,1), 1.25 (t,3), 0.88 (d,3), 0.80 (d,2).

The ethyl (4S)-4-amino-2,2-difluoro-3-hydroxy-5-methylhexanoate hydrobromide used in Example 1.g. was prepared as follows:

To a solution of ethyl (4S)-4-benzyloxycarbonylamino-2,2-difluoro-3-hydroxy-5-methylhexanoate (30.04 g, prepared as described in European Patent Application, Publication No. 397 427 A1, Example 1f; see also, U.S. Pat. No. 4,880,780, Example 1) in glacial acetic acid (200 mL) was added a solution of 30% (w/w) hydrogen bromide in acetic acid (75 mL). The mixture was allowed to stir for 2.5 hours and was evaporated to a paste. The residue was evaporated twice from toluene and the resulting solids were triturated with diethyl ether. The solids were washed with diethyl ether and dried under vacuum to give the hydrobromide salt (13.85 g) as a light brown powder; 300 MHz NMR (DMSO-$d_6$/trifluoroacetic acid): 0.96 (m,6), 1.30 (t,2, J=8.5), 2.04 (m,1), 3.20 (m,2), 4.21 (m,1), 4.35 (m,2); MS: m/z=226(M+ 1).

h. 2-(3-Benzyloxycarbonylamino-2-oxo-6-phenyl-1,2-dihydro-1-pyridyl)-N-[3,3-difluoro-2-hydroxy-1-isopropyl-3-(N-phenethylcarbamoyl)propyl]acetamide To a solution of the product from Example 1.g. (2.1 g) in ethanol (25 mL) was added phenethylamine (1.80 mL). After the 4 hours, a precipitate prevented stirring. Stirring was restarted on addition of ethanol (10 mL) and was continued overnight. The mixture was evaporated to give a paste, which was dissolved in ethyl acetate, washed (10% hydrochloric acid, brine), dried, and evaporated to yield the product amide (2.40 g) as a foam; TLC: $R_f$=0.25, dichloromethane:methanol (99:1); 300 MHz NMR: 8.59 (s,1), 8.39 (t,1), 7.95 (d,1), 7.80 (d,1), 7.47–7.15 (m,15), 6.25 (d,1), 6.06 (d,1), 5.25–5.14 (m,2), 4.45 (q,2), 4.25–4.11 (m,1), 3.73 (t,1), 3.39–3.14 (m,2), 2.73 (t,2), 1.79–1.68 (m,1), 0.85 (d,3), 0.77 (d,3MS: m/z=661(M+1).

i. 2-(3-Benzyloxycarbonylamino -2-oxo-6-phenyl-1,2-dihydro-1-pyridyl)-N-[3,3-difluoro-1-isopropyl-2-oxo-3-(N-phenethylcarbamoyl)-propyl]acetamide To a solution of the product from Example 1.h. (0.561 g) in 1:1 dimethylsulfoxide:toluene (6 mL) was added 1-(3-dimethylaminopropyl)-3-ethylcarbodiimide hydrochloride (1.63 g) and dichloroacetic acid (0.28 mL). After 2.5 hours, the yellow solution was diluted with ethyl acetate, washed (10% hydrochloric acid, saturated sodium bicarbonate, brine), dried and evaporated. The crude material was purified by chromatography, with chloroform:ether (gradient, 95:5, 90:10) as the eluent, to give the ketone (0.456 g); TLC: $R_f$=0.20, dichloromethane:methanol (99:1); 300 MHz NMR: 9.20 (t,1), 8.51–8.48 (m,2), 7.90 (d,1), 7.45–7.17 (m,15), 6.22 (d,1), 5.19 (s,2), 4.82–4.78 (m,1), 4.49 (broad s,2), 3.43–3.29 (m,2), 2.76 (t,2), 2.25–2.14 (m,1), 0.84 (d,3), 0.73 (d,3) MS: m/z=659(M+1). It is noted that this ketone is also a Compound of the invention.

EXAMPLE 2

N-[3,3-Difluoro-1-isopropyl-2-oxo-3-(N-phenethylcarbamoyl)propyl]-2-[3-(6-methylpyrid-2-ylmethoxycarbonylamino)-2-oxo-6-phenyl-1,2-dihydro-1-pyridyl]acetamide N-[3,3-Difluoro-2-hydroxy-1-isopropyl-3-(N-phenethylcarbamoyl)propyl]-2-[3-(6-methylpyrid-2-ylmethoxycarbonylamino)-2-oxo-6-phenyl-1,2-dihydro-1-pyridyl]acetamide was oxidized using a procedure similar to that described in Example 1.i., but omitting the hydrochloric acid wash. The crude material was purified by chromatography, with methanol:chloroform (1:99) as the eluent. The resulting material was triturated with diethyl ether and petroleum ether to give a solid which was triturated with petroleum ether to yield the title compound; TLC: $R_f$=0.31, chloroform:methanol (30:1); 300 MHz NMR: 9.20 (t,1), 8.68 (s,1), 8.50 (d,1), 7.91 (d,1), 7.71 (t,1), 7.48–7.11 (m,14), 6.22 (d,1), 5.18 (s,2), 4.83–4.75 (m,1), 4.50 (broad s,2), 2.76 (t,2), 2.27–2.12 (m,1), 8.48 (d,3), 7.36 (d,3); MS: m/z=674(M+1). Analysis for $C_{37}H_{37}F_2N_5O_6$: Calculated: C, 64.18; H, 5.54; N, 10.40; Found: C, 64.21; H, 5.72; N, 10.10.

The starting material alcohol was prepared as follows.

a. 2-(3-Benzyloxycarbonylamino-2-oxo-6-phenyl-1,2-dihydro-1-pyridyl)-N-[2-tert-butyldimethylsilyloxy-3,3-difluoro-1-isopropyl-3-(N-phenethylcarbamoyl)propyl]acetamide To a solution of 2-(3-benzyloxycarbonylamino-2-oxo-6-phenyl-1,2-dihydro-1-pyridyl)-N-[3,3-difluoro-2-hydroxy-1-isopropyl-3-(N-phenethylcarbamoyl)propyl]acetamide (1.83 g) in dichloromethane (28 mL) was added 2,6-lutidine (0.71 mL). The solution was cooled in an ice water bath for 15 minutes prior to the addition of tert-butyldimethylsilyl trifluoromethylsulfonate (1.31 mL). The mixture was stirred at 5° C. for 10 minutes and was allowed to warm to room temperature. After 1.5 hours, the reaction was diluted with dichloromethane (100 mL) and shaken with brine (50 mL). The organic layer was dried and evaporated. Chromatography, with chloroform:ether (gradient, 97:3, 95:5, 92:8) as the eluent, yielded the tert-butyldimethylsilyl ether (1.72 g); TLC: $R_f$=0.35, chloroform:ether (95:5); 300 MHz NMR: 8.67 (s,1), 8.26 (t,1), 7.95 (d,1), 7.52–7.12 (m,17), 6.30 (d,1), 5.17 (d,2), 4.55 (d,1), 4.38 (t,2), 3.62 (t,1), 3.20–3.03 (m,1), 2.83–2.60 (m,2), 1.83–1.67 (m,1) 0.90–0.75 (m,19), 0.097 (s,3), 0.076 (s,3); MS: m/z=775 (M+1).

b. 2-(3-Amino-2-oxo-6-phenyl-1,2-dihydro-1-pyridyl)-N-[2-tert-butyldimethylsilyloxy-3,3-difluoro-1-isopropyl-3-(N-phenethylcarbamoyl)propyl]acetamide To a solution of the product from Example 2.a. (1.01 g) in tetrahydrofuran (10 mL) was added 10% (w/w) palladium on carbon (0.21 g). The mixture was stirred under hydrogen for 5.5 hours. The mixture was filtered through diatomaceous earth, and the filter cake was washed with ethanol. The filtrate was evaporated and dried under vacuum. The crude product (0.817 g) was dissolved in chloroform and filtered through a fresh plug of diatomaceous earth. Evaporation of the filtrate gave the product (0.803 g) as a foam, which was used without further purification; TLC: $R_f$=0.33, dichloromethane:methanol (95:5); 300 MHz NMR: 0.10 (s,3), 0.11 (s,3), 0.71–0.95 (m,18), 1.63–1.84 (m,1), 2.63–2.84 (m,2), 2.97–3.13 (m,1), 3.65 (t,1), 4.12–4.16 (m,3), 5.29 (d,2), 7.12–7.50 (m,11), 8.45 (t,1); MS: m/z=641(M+1).

c. N-[2-tert-Butyldimethylsilyloxy-3,3-difluoro-1-isopropyl-3-(N-phenethylcarbamoyl)propyl]-2-[3-(6-methylpyrid-2-ylmethoxycarbonylamino)-2-oxo-6-phenyl-1,2-dihydro-1-pyridyl]acetamide To a solution of the product from Example 2.b. (0.4 g) in tetrahydrofuran (4 mL) was added triethylamine (0.26 mL). The light yellow solution was cooled to 5° C. with an ice water bath. A solution of triphosgene (65 mg) in tetrahydrofuran (1.5 mL) was added dropwise over a 5 minute period causing a mild warming. The mixture was stirred at 5° C. for 1.5 hours, and a solution of 6-methyl-2-pyridinemethanol (0.16 g) in tetrahydrofuran (1.5 mL) was added dropwise. The yellow suspension was stirred at 5° C. for 0.5 hour, and was then allowed to warm to room temperature overnight. The reaction was diluted with ethyl acetate, washed (saturated sodium bicarbonate, water, brine), dried, and evaporated. The crude product (0.48 g) was combined with the crude product (0.47 g) of another iteration of the above procedure and was purified by chromatography, eluting with, first column, chloroform:tetrahydrofuran (95:5); second column, dichloromethane:tetrahydrofuran (90:10), to yield the carbamate (0.602 g); TLC: $R_f$=0.30, chloroform:tetrahydrofuran (90:10); 300 MHz NMR: 8.83 (s,1), 8.28 (t,1), 7.99 (d,1), 7.65 (t,1), 7.53–7.01 (m,15), 6.29 (d,1), 5.16 (d,2), 4.55 (d,1), 4.37–4.31 (m,1), 3.67 (t,1), 3.20–3.06 (m,1), 2.75–2.70 (m,1), 2.44 (m,4), 1.80–1.68 (m,1), 1.35 (s,3), 0.93–7.21 (m,16), 0.09 (s,3), 0.07(s,3); MS: m/z=790(M+1).

d. N-[3,3-Difluoro-2-hydroxy-1-isopropyl-3-(N-phenethylcarbamoyl)propyl]-2-[3-(6-methylpyrid-2-ylmethoxycarbonylamino)-2-oxo-6-phenyl-1,2-dihydro-1-pyridyl]acetamide To a solution of the product from Example 2.c. (0.53 g) in tetrahydrofuran (7 mL) was added a solution of tetrabutylammonium fluoride (0.67 mL, 1M in tetrahydrofuran). The clear yellow solution was stirred at room temperature until starting material was consumed. The reaction mixture was diluted with dichloromethane (100 mL), washed (water, brine), dried and evaporated to yield the crude product as a yellow foam. Chromatography, with dichloromethane:methanol (gradient, 99:1, 98:2, 97:3) as the eluent, gave the alcohol (0.47 g); TLC: $R_f$=0.24, dichloromethane:methanol (98:2); 300 MHz NMR: 8.75 (s,1), 8.42–8.37 (t,1), 7.95 (d,1), 7.80 (d,1), 7.67 (t,1), 7.50–7.12 (m,13), 6.25 (d,1), 6.07 (d,1), 5.17 (s,2), 4.60–4.33 (broad q,2), 4.23–4.07 (m,1), 3.74 (t,1), 3.26–3.14 (m,2), 2.73 (t,2), 2.46 (s,3), 1.79–1.64 (m,1), 0.854 (d,3), 0.778 (d,3); MS: m/z=677(M+1).

EXAMPLES 3–6

The following compounds of formula I wherein $R^O$ is isopropyl, R is hydrogen, $R^5$ is hydrogen, $R^6$ is phenyl, and $R^A$ is the indicated group were prepared from the corresponding compounds of formula I wherein R is benzyloxycarbonyl using procedures similar to that described in Example 1.

EXAMPLE 3

$R^A$=4-bromophenethyl: Purified by trituration with ether; TLC: $R_f$=0.29, chloroform:methanol (20:1); MS: m/z=603 (M+1) for $^{79}$Br. Analysis for $C_{28}H_{29}BrF_2N_4O_4$: Calculated: C, 55.73; H, 4.84; N, 9.28; Found: C, 55.56; H, 4.84; N, 9.00.

EXAMPLE 4

$R^A$=4-pyridylmethyl: Purified by trituration with ether followed by chromatography, with chloroform:methanol (gradient 20:1, 10:1) as the eluent; TLC: $R_f$=0.39, chloroform:methanol (10:1); MS: m/z=512(M+1). Analysis for $C_{26}H_{27}F_2N_5O_4$.0.3 $H_2O$: Calculated: C, 60.41; H, 5.38; N, 13.55; Found: C, 60.31; H, 5.36; N, 13.29.

EXAMPLE 5

$R^A$=propyl: Purified by trituration with ether; TLC: $R_f$=0.23, chloroform:methanol (98:2); MS: m/z=463(M+1). Analysis for $C_{23}H_{28}F_2N_4O_4$.0.2 $H_2O$: Calculated: C, 59.27; H, 6.14; N, 12.02; Found: C, 59.11; H, 6.16; N, 11.88.

EXAMPLE 6

$R^A$=4-fluorobenzyl: Purified by chromatography, with chloroform:methanol (40:1) as the eluent; TLC: $R_f$=0.38, dichloromethane:methanol (95:5); MS: m/z=529(M+1). Analysis for $C_{27}H_{27}F_3N_4O_4$.0.1 $H_2O$: Calculated: C, 60.13; H, 5.27; N, 10.39; Found: C, 60.36; H, 4.93; N, 10.06.

The starting materials for Examples 3–6 were prepared as follows.

EXAMPLES 3.a.–6.a.

The following alcohols of formula II, wherein $R^O$ is isopropyl, R is benzyloxycarbonyl, $R^5$ is hydrogen, $R^6$ is phenyl and $R^A$ is the indicated group were prepared from 2-(3-benzyloxycarbonylamino-2-oxo-6-phenyl-1,2-dihydro-1-pyridyl)-N-(3,3-difluoro-3-ethoxycarbony-2-hydroxy-1-isopropyl)acetamide and the requisite amine of formula $H_2NR^A$ using procedures similar to that described in Example 1.h., except as noted.

EXAMPLE 3.a.

$R^A$=4-bromophenethyl: Used without purification; TLC: $R_f$=0.44, chloroform:methanol (20:1); MS: m/z=739(M+1) for $^{79}$Br.

EXAMPLE 4.a.

$R^A$=4-pyridylmethyl: Solids were collected by filtration. The filtrate was evaporated and the residue was dissolved in ethyl acetate, washed (saturated ammonium chloride, saturated sodium bicarbonate), dried and evaporated to yield a solid, which was combined with the material isolated by filtration; TLC: $R_f$=0.28, chloroform:methanol (20:1); MS: m/z=648(M+1).

EXAMPLE 5.a.

$R^A$=propyl: Used without purification; TLC: $R_f$=0.19, dichloromethane:methanol (98:2); MS: m/z=599(M+1).

EXAMPLE 6.a.

$R^A$=4-fluorobenzyl: The crude material was diluted with water and acidified with 10% hydrochloric acid. The ethanol was evaporated, and the resultant precipitate was filtered and washed with 10% hydrochloric acid. The solid was triturated with ether, dissolved in ethyl acetate and washed (10% hydrochloric acid, brine). The organic layer was dried and evaporated to yield the product, which was used without further purification; TLC: $R_f$=0.34, chloroform:methanol (40:1); MS: m/z=665(M+1).

EXAMPLES 3.b.–6.b.

The following compounds of formula I wherein R is benzyloxycarbonyl, $R^5$ is hydrogen, $R^6$ is phenyl and $R^A$ is the indicated group were prepared from the corresponding alcohols of formula II using a procedure similar to that described in Example 1.i. with exceptions as noted. It is noted that these products are also Compounds of the invention.

EXAMPLE 3.b.

$R^A$=4-bromophenethyl: The 10% hydrochloric acid wash was eliminated from the workup. The crude product was purified by chromatography, with chloroform:methanol (50:1); as the eluent; TLC: $R_f$0.25, chloroform:methanol (50:1); MS: m/z=737(M+1) for $^{79}$Br.

EXAMPLE 4.b.

$R^A$=4-pyridylmethyl: The 10% hydrochloric acid wash was eliminated from the workup. The crude product was purified by chromatography, with chloroform:methanol (gradient, 40:1, 20:1) as the eluent; TLC: $R_f$=0.30, chloroform:methanol (20:1); MS: m/z=646(M+1).

EXAMPLE 5.b.

$R^A$=propyl: Purified by chromatography, with chloroform:ether (gradient, 95:5, 90:10) as the chant; TLC: $R_f$=0.27, dichloromethane:methanol (99:1); MS: m/z:597 (M+1).

EXAMPLE 6.b.

$R^A$=4-fluorobenzyl: Purified by chromatography, with chloroform:methanol (40:1) as the eluent; TLC: $R_f$=0.21, chloroform:methanol (40:1); MS: m/z=663(M+1).

EXAMPLES 7–13

The following compounds of formula I wherein $R^O$ is isopropyl, R is hydrogen, $R^5$ is hydrogen, $R^6$ is phenyl, and $R^A$ is the indicated group were prepared from the corresponding compounds of formula I wherein R is benzyloxycarbonyl using procedures similar to that described in Example 1 or Example 2.b. as indicated.

EXAMPLE 7

$R^A$=2-morpholinoethyl: As described in Example 2.b. except using tetrahydrofuran (5 mL):ethanol (5 mL); chromatography with chloroform:methanol (gradient, 97:3, 96:4, 94:6); TLC: $R_f$=0.21, dichloromethane:methanol (96:4); MS: m/z=534(M+1). Analysis for $C_{26}H_{33}F_2N_5O_5 \cdot 0.2$ $CHCl_3$: Calculated: C, 56.45; H, 6.00; N, 12.56; Found: C, 56.45; H, 5.99; N, 12.53.

EXAMPLE 8

$R^A$=2-(N,N-dimethylamino)ethyl: As described in Example 1; chromatography with chloroform:methanol: concentrated ammonium hydroxide (gradient, 93.5:6:0.5, 91.5:8:0.5, 89.5:10:0.5); TLC: $R_f$=0.28, chloroform:methanol:concentrated ammonium hydroxide (89.5:10:0.5); MS: m/z=492(M+1). Analysis for $C_{24}H_{31}F_2N_5O_4$: Calculated: C, 58.68; H, 6.36; N, 14.25; Found: C, 58.54; H, 6.58; N, 13.46.

EXAMPLE 9

$R^A$=2-methoxycarbonylethyl: As described in Example 2.b. except using tetrahydrofuran (4 mL):methanol (1 mL); chromatography with chloroform:methanol (98:2); recovered material triturated with petroleum ether and diethyl ether; TLC: $R_f$=0.18, dichloromethane:methanol (97:3); MS: m/z=507(m+1). Analysis for $C_{24}H_{28}F_2N_4O_6$: Calculated: C, 56.91; H, 5.57; N, 11.06; Found: C, 56.90; H, 5.58; N, 10.87.

EXAMPLE 10

$R^A$=4-methoxycarbonylbenzyl: As described in Example 2.b. except using tetrahydrofuran (3 mL):methanol (1 mL); chromato-graphy with dichloromethene:methenol (97:3); recovered material crystallized from ethyl acetate:hexane; TLC: $R_f$=0.29, dichloromethane:methanol (96:4); MS: m/z=569(M+1). Analysis for $C_{29}H_{30}F_2N_4O_6$: Calculated: C, 61.26; H, 5.32; N, 9.85; Found: C, 61.15; H, 5.39; N, 9.75.

EXAMPLE 11

$R^A$=4-fluorobenzyl: As described in Example 2.b. except used 30% by weight catalyst, single filtration through diatomaceous earth, and not purified further; TLC: $R_f$=0.15, chloroform:methanol (40:1); MS: m/z=529(M+1).

EXAMPLE 12

$R_A$=2-(4-methoxycarbonylphenyl)ethyl: As described in Example 2.b. except used 30% by weight catalyst, solvent was ethanol:tetrahydrofuran (2:1), and single filtration. Chromatography solvent: dichloromethane:methanol (95:5); TLC: $R_f$=0.45, dichloromethane:methanol (95:5); MS: m/z=583(M+1). Analysis for $C_{30}H_{32}N_4O_6F_2$: Calculated: C, 61.85; H, 5.54; N, 9.62; Found: C, 61.64; H, 5.68; N, 9.42.

EXAMPLE 13

$R^A$=2-(4-pyridyl)ethyl: As described in Example 2.b. except used 30% by weight catalyst; solvent was ethanol:tetrahydrofuran (2:1); reaction mixture was filtered and resubjected to the reaction conditions with 20% catalyst; and single filtration. Chromatography solvent: dichloromethane:methanol (95:5); TLC: $R_f$=0.11, dichloromethane:methanol (95:5); MS: m/z=526(M+1). Analysis for $C_{27}H_{29}F_2N_5O_4 \cdot 0.80$ $H_2O$: Calculated: C, 60.06; H, 5.71; N, 12.97; Found: C, 60.04; H, 5.35; N, 12.76.

EXAMPLES 7.a.–13.a.

The following alcohols of formula II, wherein $R^O$ is isopropyl, R is benzyloxycarbonyl, $R^5$ is hydrogen, $R^6$ is phenyl and $R^A$ is the indicated group were prepared from 2-(3-benzyloxycarbonylamino-2-oxo-6-phenyl-1,2-dihydro-1-pyridyl)-N-(3,3-difluoro-3-ethoxycarbonyl-2-hydroxy-1-isopropyl)acetamide and the requisite amine of formula $H_2NR^A$ using procedures similar to that described in Example 1.h., except as noted.

EXAMPLE 7.a.

$R^A$=2-morpholinoethyl: Washed (water, brine); TLC: $R_f$=0.17, dichloromethane:methanol (98:2); MS: m/z=670 (M+1).

EXAMPLE 8.a.

$R^A$=2-(N,N-dimethylamino)ethyl: Washed (water, brine); TLC: $R_f$=0.21, chloroform:methanol (2×98:2); MS: m/z=628(M+1).

EXAMPLE 9.a.

$R^A$=2-methoxycarbonylethyl: Except added triethylamine (2.18 mL) and stirred 3 days; chromatography with chloroform:methanol (gradient, 99:1, 98:2, 95:5); TLC: $R_f$=0.41, chloroform:methanol (97:3); MS: m/z=643(M+1).

EXAMPLE 10.a.

$R^A$=4-methoxycarbonylbenzyl: Except added triethylamine (2.4 mL) and stirred 3 days. After evaporating the reaction mixture, the residue was suspended in ethyl acetate and washed (10% hydrochloric acid). The solids were washed (water, diethyl ether) and dried under vacuum to give the product as a white solid; TLC: $R_f$=0.38, dichloromethane:methanol (97:3); MS: m/z=705(M+1).

EXAMPLE 11.a.

$R^A$=4-fluorobenzyl: Diluted with water; pH adjusted to 6–7 with 10% hydrochloric acid, then evaporated. Resulting solid was filtered, dissolved in ethyl acetate, washed (10% hydrochloric acid, brine) and used without further purification; TLC: $R_f$=0.28, chloroform:methanol (40:1); MS: m/z=665(M+1).

EXAMPLE 12.a.

$R^A$=2-(4-methoxycarbonylphenyl)ethyl: Diluted with water; pH adjusted to 6–7 with 10% hydrochloric acid, then evaporated, Chromatography solvent: dichloromethane: ethyl acetate (gradient 90:10, 85:5, 80:20); TLC: $R_f$=0.09, dichloromethane:methanol (90:10); MS: m/z=719(M+1).

EXAMPLE 13.a.

$R^A$=2-(4-pyridyl)ethyl: Diluted with water and evaporated; the resulting oil was purified by hexane precipitation; TLC: $R_f$=0.21, chloroform:methanol (40:1); MS: m/z=662 (M+1).

EXAMPLE 7.b.–13.b.

The following compounds of formula I wherein R is benzyloxycarbonyl, $R^5$ is hydrogen, $R^6$ is phenyl and $R^A$ is the indicated group were prepared from the corresponding alcohols of formula II using a procedure similar to that described in Example 1.i. with exceptions as noted. It is noted that these products are also Compounds of the invention.

EXAMPLE 7.b.

$R^A$=2-morpholinoethyl: Washed (saturated sodium bicarbonate, brine); chromatography with chloroform: methanol (gradient, 99:1, 98:2, 97:3, 95:5); TLC: $R_f$=0.32, dichloromethane:methanol (97:3); MS: m/z=668(M+1). Analysis for $C_{34}H_{39}F_2N_5O_7$·0.4 $H_2O$: Calculated: C, 60.51; M, 5.94; N, 10.38; Found: C, 60.52; H, 5.79; N, 10.29.

EXAMPLE 8.b.

$R^A$=2-(N,N-dimethylamino)ethyl: Washed (saturated sodium bicarbonate, brine); chromatography with dichloromethane:methanol (gradient, 98:2, 97:3, 96:4, 94:6, 92:8); TLC: $R_f$=0.19, dichloromethane:methanol (95:5); MS: m/z= 626. Analysis for $C_{32}H_{37}F_2N_5O_6$·0.5 $H_2O$: Calculated: C, 60.56; H, 6.03; N, 11.03; Found: C, 60.67; H, 5.95; N, 10.96.

EXAMPLE 9.b.

$R^A$=2-methoxycarbonylethyl: First chromatography with chloroform:methanol (gradient, 99:1, 98:2, 95:5); second chromatography using Waters Prep 500(trademark) HPLC system (silica) with hexane:ethyl acetate (7:3), then ethyl acetate; TLC: $R_f$=0.21, hexane:ethyl acetate:diethylether (5:3:2); MS: m/z=641(M+1). Analysis for $C_{32}H_{34}F_2N_4O_8$: Calculated: C, 60.00; H, 5.35; N, 8.75; Found: C, 60.27; H, 5.50; N, 8.60.

EXAMPLE 10.b.

$R^A$=4-methoxycarbonylbenzyl: Triturated with ethyl acetate:hexane; TLC: $R_f$=0.41, dichloromethane:methanol (98:2); MS: m/z=703(M+1). Analysis for $C_{37}H_{36}F_2N_4O_8$: Calculated: C, 63.24; H, 5.16; N, 7.97; Found: C, 63.14; H, 5.22; N, 7.93.

EXAMPLE 11.b.

$R^A$=4-fluorobenzyl: Chromatography solvent: chloroform:methanol (40:1); TLC: $R_f$=0.30, chloroform:methanol (40:1); MS: m/z=663(M+1).

EXAMPLE 12.b.

$R^A$=2-(4-methoxycarbonylphenyl)ethyl: No acid wash done. Chromatography solvent: dichloromethane:ethyl acetate (gradient 90:10, 85:5); TLC: $R_f$=0.32, dichloromethane:ethyl acetate (90:10); MS: m/z=717(M+1).

EXAMPLE 13.b.

$R^A$=2-(4-pyridyl)ethyl: No acid wash done. Chromatography solvent: dichloromethane:methanol (gradient 97:3, 96:4); TLC: $R_f$=0.40, dichloromethane:methanol (95:5); MS: m/z=660(M+1). Analysis for $C_{35}H_{35}F_2N_5O_6$·0.5 $H_2O$: Calculated: C, 62.87; H, 5.42; N, 10.49; Found: C, 62.87; H, 5.32; N, 10.45.

EXAMPLES 14–15

The following compounds of formula I wherein $R^O$ is isopropyl, R is hydrogen, $R^5$ is hydrogen, $R^6$ is 4-fluorophenyl, and $R^A$ is the indicated group were prepared from the corresponding compounds of formula I wherein R is benzyloxycarbonyl using procedures similar to that described in Example 1.

EXAMPLE 14

$R^A$=propyl: Trituration of the crude product with ether gave the title compound as an off white powder; TLC: $R_f$=0.31, chloroform:methanol (97:3); 300 MHz NMR: 9.09 (t,1), 8.43 (d,1), 7.34 (m,2), 7.21 (m,2), 6.50 (d,1), 5.97 (d,1), 5.19 (s,2), 4.80 (m,1), 4.44 (m,2), 3.08 (m,2), 2.21 (m,1), 1.45 (m,1), 0.80 (m,9); MS: m/z=481(M+1). Analysis for $C_{23}H_{27}F_3N_4O_4$: Calculated: C, 57.49; H, 5.67; N, 11.66; Found: C, 57.42; H, 5.65; N, 11.64.

EXAMPLE 15

$R^A$=phenethyl: Chromatography with chloroform:methanol (98:2); TLC: $R_f$=0.18, chloroform:methanol (98:2); MS: m/z=543(M+1). Analysis for $C_{28}H_{29}F_3N_4O_4$: Calculated: C, 61.98; H, 5.39; N, 10.33; Found: C, 61.98; H, 5.48; N, 10.08.

The urethanes needed for the above examples were prepared as follows.

EXAMPLES 14.a.–14.g. (also starting material for Example 15.h.)

2-[3-Benzyloxycarbonylamino-6-(4-fluorophenyl)-2-oxo-1,2-dihydro-1-pyridyl]-N-(3,3-difluoro-3-ethoxycarbonyl-2-hydroxy-1-isopropyl)acetamide was prepared using procedures similar to those described in Examples 1.a.–1.g., except that 4-fluoroacetophenone was used instead of acetophenone. The corresponding intermediates are described below.

EXAMPLE 14.a.

3-Aza-4-(4-fluorophenyl)pent-3-enal dimethyl acetal

Fractional distillation gave three major fractions: fraction 1 (75°–109° C., 40 Pa); fraction 2 (110–113° C., 40 Pa); fraction 3 (110°–90° C., 33 Pa). Fraction 1 contained 12% 4-fluoroacetophenone. Fraction 2 and fraction 3 contained less than 1% 4-fluoroacetophenone and acetal.

EXAMPLE 14.b.

Dimethyl 4-aza-3-(4-fluorophenyl)-6,6-dimethoxyhex-2-enylidenemalonate

The mixture was diluted with dichloromethane, washed (saturated ammonium chloride, brine), dried and evaporated, followed by chromatography with chloroform:ethyl acetate (gradient, 20:1, 10:1, 5:1, 5:3) as the eluent, to give the title compound; TLC: $R_f$=0.26, chloroform:ethyl acetate (40:1), developed twice; MS: m/z=368(M+1).

EXAMPLE 14.c.

1-(2,2-Dimethoxy)-6-(4-fluorophenyl)pymid-2-one-3-carboxylic acid

Used without purification; TLC: $R_f$=0.40, dichloromethane:methanol:acetic acid (96.5:3:0.5); MS: m/z=322 (M+1).

EXAMPLE 14.d.

3-Benzyloxycarbonylamino-6-(4-fluorophenyl)-2-oxo-1,2-dihydro-1-pyridylacetaldehyde dimethyl acetal The residual oil was dissolved in ethyl acetate, washed (10% hydrochloroic acid, saturated sodium bicarbonate, brine), dried and evaporated. Chromatography, eluting with chloroform:ethyl acetate (98:2), gave the acetal; TLC: $R_f$=0.23, chloroform:ethyl acetate (95:5); MS: m/z=427(M+1).

EXAMPLE 14.e.

3-Benzyloxycarbonylamino-6-(4-fluorophenyl)-2-oxo-1,2-dihydro-1-pyridylacetaldehyde Procedure: The reaction mixture was held at reflux for 1 hour to give a yellowish solution. After cooling, the solution was diluted with chloroform and saturated aqueous sodium bicarbonate was added until the aqueous layer was pH 8. The layers were separated and the aqueous portion was extracted with chloroform. The combined chloroform extracts were dried, evaporated, and dried under vacuum. Trituration with ether gave the aldehyde as a white solid; TLC: $R_f$=0.33, chloroform:ethyl acetate; MS: m/z=381(M+1).

EXAMPLE 14.f.

3-Benzyloxycarbonylamino-6-(4-fluorophenyl)-2-oxo-1,2-dihydro-1-pyridylacetic acid Used without purification; TLC: $R_f$=0.11, chloroform:methanol:acetic acid (98.5:1:0.5); MS: m/z=397(M+1).

EXAMPLE 14.g.

2-[3-Benzyloxycarbonylamino-6-(4-fluorophenyl)-2-oxo-1,2-dihydro-1-pyridyl]-N-(3,3-difluoro-3-ethoxycarbonyl-2-hydroxy-1-isopropyl)acetamide Chromatography with chloroform:methanol (gradient, 99:1, 98.5:1.5); TLC: $R_f$=0.23, dichloromethane:methanol (99:1); MS: m/z=604(M+1).

EXAMPLES 14.h.–15.h.

The following alcohols of formula II, wherein $R^O$ is isopropyl, R is benzyloxycarbonyl, $R^5$ is hydrogen, $R^6$ is 4-fluorophenyl and $R^A$ is the indicated group were prepared from 2-[3-benzyloxycarbonylamino-6-(4-fluorophenyl)-2-oxo-1,2-dihydro-1-pyridyl]-N-(3,3-difluoro-3-ethoxycarbonyl-2-hydroxy-1-isopropyl)-acetamide and the requisite similar to that $H_2NR^A$ using procedures similar to that described in Example 1.h., except as noted.

EXAMPLE 14.h.

$R^A$=propyl: Chromatography with chloroform:ether (9:1) followed by chloroform:methanol (99:1); TLC: $R_f$=0.31, dichloromethane:methanol (98:2); MS: m/z=679(M+1).

EXAMPLE 15.h.

$R^A$=phenethyl: Trituration of the crude product with ether:hexane gave the alcohol as a white solid; TLC: $R_f$=0.47, chloroform:methanol (98:2); MS: m/z=679(M+1).

EXAMPLES 14.i.–15.i.

The following compounds of formula I wherein R is benzyloxycarbonyl, $R^5$ is hydrogen, $R^6$ is 4-fluorophenyl and $R^A$ is the indicated group were prepared from the corresponding alcohols of formula II using a procedure similar to that described in EXAMPLE 1.i. with exceptions as noted. It is noted that these products are also Compounds of the invention.

EXAMPLE 14.i.

$R^A$=propyl: Chromatography with chloroform:ethyl acetate (9:1); TLC: $R_f$=0.18, chloroform:ethyl acetate (9:1); MS: m/z=615(M+1).

EXAMPLE 15.i.

R=4-fluorophenyl, $R^A$=phenethyl: Chromatography with chloroform:methanol (99:1); TLC: $R_f$=0.35, chloroform:methanol (99:1); MS: m/z=677(M+1).

EXAMPLE 16

2-(3-Trifluoroacetylamino-2-oxo-6-phenyl-1,2-dihydro-1-pyridyl)-N-[3,3-difluoro-1-isopropyl-3-[N-(2-morpholinoethyl)carbamoyl]propyl]acetamide To a solution of 2-(3-amino-2-oxo-6-phenyl-1,2-dihydro-1-pyridyl)-N-[3,3-difluoro-1-isopropyl-3-[N-(2-morpholinoethyl)carbamoyl]propyl]acetamide (0.27 g) in dichloromethane (5 mL) was added trifluoroacetic anhydride (0.105 mL). After 2 hours the solution was evaporated to give a crude oil. The oil was purified by chromatography, twice; (first column) with dichloromethane:methanol (gredient, 98:2, 97:3, 96:4) as the eluent and (second column) with ethyl acetate:ether (6:4) and chloroform:methanol (95:5) as the eluent. The resulting material was triturated with hexane and ether to give the title compound as a tan solid (0.092 g); TLC: $R_f$=0.38, ethyl acetate:ether (7:3); NMR: 10.39 (s,1), 9.04 (broad s,1), 8.52 (d,1), 8.01 (d,1), 7.52–7.37 (m,5), 6.29 (d,1), 4.82 (m,1), 4.52 (s,2), 3.54 (m,4), 3.26 (m,2), 2.35–2.21 (m,7), 0.86 (d,3), 0.74 (d,3); MS: m/z=630 (M+I). Analysis for $C_{28}H_{32}F_5N_5O_6 \cdot 0.3 H_2O$: Calculated: C, 52.96; H, 5.17; N, 11.03: Found: C, 53.07; H, 5.14; N, 10.73.

EXAMPLES 17–18

The following compounds of formula I wherein $R^O$ is isopropyl, R is trifluoroacetyl, $R^5$ is hydrogen, $R^6$ is 4-fluorophenyl, and $R^A$ is the indicated group were prepared from the corresponding compounds of formula I wherein R is hydrogen using procedures similar to that described in Example 16, except as noted.

EXAMPLE 17

$R^A$=propyl: Triethylamine (0.21 mL) was added in an acylation of 0.103 g of the 3-aminopyridone. The reaction mixture was diluted with dichloromethane, washed (10% hydrochloric acid, saturated sodium bicarbonate, brine), dried, and evaporated. Chromatography, with chloroform: ethyl acetate (9:1) as the eluent, followed by two crystallizations from ethyl acetate and hexane gave the title compound; TLC: $R_f$=0.42, chloroform:methanol (98:2); MS: m/z=577(M+1). Analysis for $C_{25}H_{26}F_6N_4O_5$: Calculated: C, 52.08; H, 4.55; N, 9.72; Found: C, 52.08; H, 4.51; N, 9.71.

EXAMPLE 18

$R^A$=phenethyl: Triethylamine (0.20 mL) was added. The reaction was diluted with dichloromethane, washed (10% hydrochloric acid, saturated sodium bicarbonate, brine), dried, and evaporated. Chromatography, with chloroform: ethyl acetate (9:1), followed by chloroform:methanol (98:2) as the eluent, gave the title compound; TLC: $R_f$=0.48, chloroform:methanol (98:2); MS: m/z=639(M+1). Analysis for $C_{30}H_{28}F_6N_4O_5 \cdot 0.3\ H_2O$: Calculated: C, 55.95; H, 4.48; N, 8.70; Found: C, 55.98; H, 4.47; N, 8.59.

EXAMPLE 19

2-(3-Acetylamino-2-oxo-6-phenyl-1,2-dihydro-1-pyridyl)-N-[3,3-difluoro-1-isopropyl-3-(N-propylcarbamoyl)-2-oxopropyl]acetamide.

Using a procedure similar to that described in Example 1.i., 2-(3-acetylamino-2-oxo-6-phenyl-1,2-dihydro-1-pyridyl)-N-[3,3-difluoro-2-hydroxy-1-isopropyl-3-(N-propylcarbamoyl)propyl]acetamide was oxidized, and purified by chromatography with dichloromethane:ether:methanol (75:25:1) as eluent. The resulting material was precipitated from chloroform and ethyl acetate with ether to give the title compound as a white solid; TLC: $R_f$=0.33, dichloromethane:ether:methanol (74:25:1); NMR: 9.35 (s,1), 9.10 (t,1), 8.51 (d,1), 8.26 (d,1), 7.46–7.34 (m,5), 6.19 (d,1), 4.88 (m,1), 4.49 (m,2), 3.08 (m,2), 2.27 (m,1), 2.14 (s,3), 1.45 (m,2), 0.88–0.74 (m,9); MS: m/z=505(M+1). Analysis for $C_{25}H_{30}F_2N_2O_5$: Calculated: C, 59.51; H, 5.99; N, 11.11; Found: C, 60.33; H, 6.36; N, 10.42.

The starting material alcohol was prepared as follows:

a. 2-[3-Benzyloxycarbonylamino-6-(2-chlorophenyl)-2-oxo-1,2-dihydro-1-pyridyl]-N-[3,3-difluoro-2-hydroxy-1-isopropyl3-(Npropylcarbamoyl)propyl]acetamide.

Using a procedure similar to that described in Example 1.h., except the reaction mixture was diluted with water, 10% hydrochloric acid was used to adjust the pH to 6–7, and the crude product was used directly, 2-[3-benzyloxycarbonylamino-6-(2-chlorophenyl)-2-oxo-1,2-dihydro-1-pyridyl]-N-(3,3-difluoro-3-ethoxycarbonyl-2-hydroxy-1-isopropyl)acetamide was treated with propylamine to afford the amide; TLC: $R_f$=0.31, dichloromethane:methanol (98:2); MS: m/z=634(M+1).

b. 2-[3-Amino-6-(2-chlorophenyl)-2-oxo-1,2-dihydro-1-pyridyl]-N-[3,3-difluoro-2-hydroxy-1-isopropyl-3-(N-propylcarbamoyl)propyl]-acetamide Using a similar procedure to that described in Example 2.b., hydrogenolysis of the benzyloxycarbonyl group of the product of Example 19.a. afforded the 3-amino compound, which was used without further purification; TLC: $R_f$=0.34, dichloromethene:methanol (97:3); MS: m/z=499(M+1).

c. 2-(3-Amino-2-oxo-6-phenyl-1,2-dihydro-1-pyridyl)-N-[3,3-difluoro-2-hydroxy-1-isopropyl-3-(N-propylcarbamoyl)propyl]acetamide To a solution of the product of Example 19.b. (0.17 g) in ethanol (3 mL) was added sodium methoxide (0.021 g) and 10% (w/w) palladium on carbon (0.055 g). The mixture was stirred under hydrogen for 6 hours. The mixture was filtered through diatomaceous earth, and the filter cake washed with ethanol. The reaction was found to be incomplete and the filtrate was concentrated to a residue. To a solution of the residue in ethanol (3 mL) was added 10% (w/w) palladium on carbon (0.055 g). The mixture was stirred under hydrogen for 24 hours. The mixture was filtered as above and evaporated to give a residue. Chromatography, with dichloromethane:ethyl acetate:methanol (gradient, 74:25:1, 72:25:3) as the eluent, yielded the 6-phenyl derivative (0.070 g); TLC: $R_f$=0.28, dichloromethane:ethyl acetate: methanol (73:25:2); MS: m/z=465(M+1).

d. 2-(3-Acetylamino-2-oxo-6-phenyl-1,2-dihydro-1-pyridyl)-N-[3,3-difluoro-2-hydroxy-1-isopropyl-3-(N-propylcarbamoyl)propyl]-acetamide To a solution of the product of Example 19.c. (0.067 g) in tetrahydrofuran (2 mL) was added triethylamine (0.021 mL) and acetyl chloride (0.010 mL). After 1.5 hours the reaction mixture was diluted with ethyl acetate, washed (10% hydrochloric acid, saturated sodium bicarbonate, brine), dried and evaporated to give the crude product, which was used without further purification; TLC: $R_f$=0.22, chloroform:methanol (98:2), developed 3 times; 300 MHz NMR: 9.36 (s,1), 8.29 (m,2), 7.76 (d,1), 7.45 (m,5), 6.20 (d,1), 6.05 (d,1), 4.44 (m,2), 4.15 (m,1), 3.75 (m,1), 3.09 (m,1), 2.94 (m,1), 2.14 (s,3), 1.72 (m,1), 1.44 (m,2), 0.87–0.78 (m,9); MS: m/z=507(M+1).

EXAMPLE 20

N[3,3-difluoro-1-isopropyl-3-(N-propylcarbamoyl)-2-oxo-propyl]-2-[2-oxo-6-phenyl-3-(4-pyridylmethoxycarbonylamino-1,2-dihydro-1-pyridyl]acetamide Using a similar procedure to that described in Example 1.i., except the acid wash was omitted, N-[3,3-difluoro-2-hydroxy-1-iso-propyl-3-(N-propylcarbamoyl)propyl]-2-[2-oxo-6-phenyl-3-(4-pyridylmethoxycarbonylamino-1,2-dihydro-1-pyridyl]acetamide was oxidized. The crude product was purified by chromatography, eluting with, first column, ether:ethyl acetate (1:1), dichloromethane:methanol (gradient, 98:2, 92:8); second column, dichloromethane:methanol (gradient, 99:1, 98:2, 95:5), to yield the title compound; TLC: $R_f$=0.24, dichloromethane:methanol (98:2); NMR: 9.10 (t,1), 8.83 (s,1), 8.57 (m,2), 8.50 (d,1), 7.91 (d,1), 7.45 (m,5), 7.36 (m,2), 6.22 (d,1), 5.24 (s,2), 4.83 (m,1), 4.50 (m,2), 3.08 (m,2), 2.25 (m,1), 1.45 (m,2), 0.88–0.74 (m,9); MS: m/z=598(M+1). Analysis for $C_{30}H_{33}F_2N_5O_6$: Calculated: C, 60.29; H, 5.57; N, 11.72; Found: C, 60.06; H, 5.88; N, 11.14.

The starting alcohol was prepared as follows:

a. N-[3,3-difluoro-2-hydroxy-1-isopropyl-3-(N-propylcarbamoyl)-propyl]-2-[2-oxo-6-phenyl-3-(4-pyridylmethoxycarbonylamino-1,2-dihydro-1-pyridyl] acetamide Using a similar procedure to that described in Example 2.c., but using 4-pyridinemethanol instead of 6-methyl-2-pyridimemethanol, and purifying by chromatography, eluting with dichloromethane:methanol (gradient, 98:2, 96:4), 2-(3-amino-2-oxo-6-phenyl-1,2-dihydro-1-pyridyl)-N-[3,3-difluoro-2-hydroxy-1-isopropyl-3-(N-propylcarbamoyl) propyl]acetamide was converted into the urethane; TLC: $R_f$=0.27, dichloromethane:methanol (98:2), developed 4 times; MS: m/z=600(M+1).

EXAMPLE 21

2-(3-Amino-2-oxo-6-phenyl-1,2-dihydro-1-pyridyl)-N-[3,3-difluoro-1-isopropyl-3-[N-[2-(4-methoxyphenyl)ethyl]carbamoyl]-2-oxopropyl] acetamide Using a procedure similar to that of Example 1 except that the product was washed with brine only, and purifying by chromatography, eluting with chloroform:methanol (gradient 50:1 to 40:1), 2-(3-benzyloxycarbonylamino-2-oxo-6-phenyl-1,2-dihydro-1-pyridyl)-N-[3,3-difluoro-1-isopropyl-3-[N-[2-(4-methoxyphenyl)ethyl]carbamoyl]-2-oxopropyl]acetamide was deprotected to afford the title compound; TLC: $R_f$=0.11, chloroform:methanol (40:1); MS: m/z=555(M+1). Analysis for $C_{29}H_{32}N_4O_5$: Calculated: C, 62.81; H, 5.82; N, 10.10; Found: C, 62.49; H, 5.90; N, 9.84.

The starting material urethane was prepared as follows.

a. 6-(2-Chlorophenyl)pyrid-2-one-3-carbonitrile

To a 5 liter, 3-necked flask equipped with a mechanical stirrer, thermometer, reflux condenser capped with a nitrogen inlet, and a heating mantle were added o-chloroacetophenone (305.8 g), N,N-dimethylformamide dimethyl acetal (707.0 g), and acetonitrile (dried over molecular sieves, 3.0 L) giving an orange solution. The mixture was heated gradually to reflux (83° C.) over 1.5 hours, then maintained at reflux for 18 hours. After the dark red solution was cooled to room temperature, the acetonitrile was evaporated, leaving a heavy red oil. The oil was redissolved in toluene (1 L). The toluene was evaporated to afford the crude enamine which was further dried under high vacuum overnight to afford 2'-chloro-3-dimethylaminopropenophenone (422 g) which was used without further purification.

To a 12-liter, 3-necked flask equipped with a mechanical stirrer, a Claisen adapter holding a thermometer and a reflux condenser capped with a nitrogen inlet, and a heating mantle were added the crude enamine (422 g) and N,N-dimethylformamide (dried over molecular sieves, 4.0 L), giving a reddish-brown solution. Cyanoacetamide (189.2 g) was added as a dry solid and washed down with N,N-dimethylformamide (500 mL). Lastly, sodium methoxide (235.1 g) was added as a dry solid and washed down with N,N-dimethylformamide (500 mL). The mixture was heated gradually over 4 hours to 130° C., then maintained at 135–140° C. for 16 hours. The effluent line from the nitrogen bubbler was trapped through a solution of 3N HCl (2 L). The cooled reaction mixture was evaporated under pump vacuum (bath temperature 50° C.) until approximately 4 liters of N,N-dimethylformamide was removed. The residue was poured into ice/water (6 L) with vigorous stirring. The pH was adjusted to pH 5 by portionwise addition of concentrated hydrochloric acid (300 mL). This produced a suspension of reddish-orange solid. The solid was collected by suction filtration, washed with cold water (2 times 1.5 L) followed by ether (3 times 500 mL), leaving a pinkish-tan powder which was dried in the vacuum oven at 60° C. to afford 6-(2-chlorophenyl)pyrid-2-one-3-carbonitrile (205.5 g); mp 242°–245° C. (dec).

b. 6-(2-Chlorophenyl)pyrid-2-one-3-carboxylic acid

To a 5 liter, 3-necked flask equipped with a mechanical stirrer, thermometer, reflux condenser capped with a nitrogen inlet, and a heating mantle were added 6-(2-chlorophenyl)pyrid-2-one-3-carbonitrile (205.5 g), 48% hydrobromic acid (1500 mL), and glacial acetic acid (1500 mL). The golden-brown suspension was heated gradually over a four hour period to gentle reflux (117° C.). During this time, all solids dissolved giving a dark brown solution. The reaction mixture was maintained at reflux for 20 hours, then cooled to room temperature and evaporated until approximately 2 liters of distillate were collected. The remaining suspension was poured into ice/water (5 L) with vigorous stirring, precipitating a tan solid. The solid was collected by suction filtration, washed with cold water (2 times 1.5 L) and dried in the vacuum oven at 60° C. to afford 6-(2-chlorophenyl)pyrid-2-one-3-carboxylic acid (189.7 g); mp 234° C. (dec).

c. 3-Benzyloxycarbonylamino-6-(2-chlorophenyl)pyrid-2-one

To a 5 liter, 3-necked flask equipped with a mechanical stirrer, a Claisen adaptor holding a thermometer and a reflux condenser capped with a nitrogen inlet, and a heating mantle were added 6-(2-chlorophenyl)pyrid-2-one-3-carboxylic acid (189.7 g) and dioxane (dried over molecular sieves, 3.0 L) at ambient temperature, giving a tan suspension. Triethylamine (92.3 g) was added in one portion and caused the solids to dissolve. Diphenylphosphoryl azide (232.0 g) was added in one portion and washed down with dioxane (100 mL). The reaction mixture was heated gradually over one hour to reflux (103° C.). At approximately 70° C., nitrogen evolution began as the intermediate acylazide began to decompose. The reaction mixture was heated at reflux for two hours (until nitrogen evolution ceased) and then was cooled to 90° C. Benzyl alcohol (dried over molecular sieves, 169.0 g) was added in one portion. The reaction mixture was heated at reflux for 45 hours. After this time, the reaction was checked by TLC using two different solvent systems: A. Dichloromethane:methanol:acetic acid (95:5:trace), $R_f$(starting acid):0.55, $R_f$(benzyl alcohol)=0.80, $R_f$(product)=0.80; and B. Dichloromethane:ethyl acetate (9:1), $R_f$(starting acid)=0–0.15, $R_f$(benzyl alcohol)=0.6, $R_f$(product):4.4. The reaction appeared complete by TLC; so the mixture was cooled to ambient temperature and stirred overnight. During this time, a crop of tan crystals precipitated. The material was collected by suction filtration, washed with dioxane (200 mL) and ether (2 times 200 mL), then dried to afford crude product (148.0 g). The filtrate was evaporated and the residue was redissolved in dichloromethane (4 L), and washed with aqueous sodium bicarbonate solution (2 times 800 mL) and brine (1 L), dried ($MgSO_4$), and evaporated leaving a brown semisolid which was triturated with ether and filtered to afford a second crop of crude product (72.5 g). Both fractions of material were shown by NMR to be contaminated with benzyl alcohol and triethylamine hydrochloride. The combined crude material (220.5 g) was stirred for five hours in a mixture of dichloromethane (2.5 L) and 1N hydrochloric acid (1 L), then filtered. The solid was washed with water (3 times 500 mL) and ether (2 times 300 mL) to afford pure product (158.0 g). The organic phases were separated from the filtrates and evaporated. The residual solid was pressure filtered through a silica gel plug (eluent: dichloromethane:ethyl acetate, 3:1) to afford a second fraction of pure product (26.5 g). Thus was obtained 3-benzyloxycarbonylamino-6-(2-chlorophenyl)pyrid-2-one (184.5 g); mp 213°–215° C.

d. 1-Allyl-3-benzyloxycarbonylamino-6-(2-chlorophenyl) pyrid-2-one

To a cold (5° C.) suspension of the product of Example 21.c. (15 g) in dimethylformamide (470 mL) was added sodium hydride (1.15 g) in three equal portions at five minute intervals. Gas evolution was noticed upon allowing the reaction to warm to room temperature. Within one hour dissolution had occurred. The solution was recooled, and allyl bromide (3.92 mL) was added dropwise over 12–15 minutes. The reaction stirred overnight, slowly coming to room temperature. The reaction was quenched with 10% hydrochloric acid (450 mL) and water (150 mL). The aqueous phase was extracted with ethyl acetate. The organic phase was washed (water, saturated sodium bicarbonate, brine), dried and evaporated. The resulting oil was dried under vacuum (40° C.) to give a solid. Ether trituration yielded a first crop of the 1-allyl compound (2.76 g). The filtrate was chromatographed eluting with hexane:ethyl acetate (gradient 8:1 to 6:1) to obtain another crop of the 1-allyl compound (5.65 g); TLC: R$_f$=0.18, hexane:ethyl acetate (6:1); MS: m/z=395(M+1).

e. 3-Benzyloxycarbonylamino-6-(2-chlorophenyl)-1-(2,3-dihydroxypropyl)pyrid-2-one To a solution of the product of Example 21.d. (8.3 g) in 10:1 tetrahydrofuran:water (200 mL) was added 4-methylmorpholine oxide (2.71 g) and osmium tetroxide (0.033 g). After 3.5 hours, additional 4-methylmorpholine oxide (1.1 g) was added. After stirring overnight, the reaction was incomplete; so additional 4-methylmorpholine oxide (0.71 g) was added. After 6.5 hours more 4-methylmorpholine oxide (0.35 g) and osmium tetroxide (catalytic amount) were added, and the reaction stirred overnight. When complete, the reaction was quenched with saturated sodium thiosulfate. Upon stirring, the reaction mixture turned dark; diatomaceous earth was added, along with more sodium thiosulfate. The mixture was filtered through more diatomaceous earth, and the cake was washed with ethyl acetate. The filtrate layers were separated. The organic phase was washed (saturated ammonium chloride, brine), dried and evaporated to afford the crude diol as an oil (9.9 g) which was utilized without purification; TLC: R$_f$=0.49, dichloromethane:methanol; MS: m/z=429(M+1).

f. 3-Benzyloxycarbonylamino-6-(2-chlorophenyl)-2-oxo-1,2-dihydro-1-pyridylacetaldehyde To a solution of the product of Example 21.e. (9.9 g) in ethanol (200 mL) was added a slurry of sodium periodate (4.96 g) in water (about 30 mL). After stirring at room temperature for three hours, the reaction mixture was filtered through diatomaceous earth which was then rinsed with ethyl acetate. The filtrate was partially evaporated, then rediluted with ethyl acetate. The solution was washed with a water:brine mixture and dried to afford the aldehyde (10 g) which was not further purified; TLC: R$_f$=0.53, dichloromethane:methanol (95:5); MS: m/z=397(M+1).

g. 3-Benzyloxycarbonylamino-6-(2-chlorophenyl)-2-oxo-1,2-dihydro-1-pyridylacetic acid The product of Example 21.f. was oxidized using a procedure similar to that described in Example 1.f. with the following slight variations. The reaction was run at room temperature. When complete, it was quenched and partially evaporated. The resulting aqueous phase was made basic to pH 9–10 with 2.5N sodium hydroxide solution and extracted with ether to remove any unreacted aldehyde. The aqueous phase was acidified to pH 2 with 10% hydrochloric acid and extracted with ethyl acetate. The organic phase was washed (brine), dried and evaporated. The residue was partially redissolved in hot hexane:ethyl acetate and the insoluble (inorganic) matter filtered from the hot solution; the filtrate was evaporated and chromatographed, eluting with dichloromethane:methanol:acetic acid (gradient 95:5:0, 9:1:0, 9:1:1, 9:1:2); to afford the acid; TLC: R$_f$0.05, dichloromethane:methanol (95:5); MS: m/z=413(M+1).

h. 2-[3-Benzyloxycarbonylamino-6-(2-chlorophenyl)-2-oxy-1,2-dihydro-1-pyridyl]-N-(3,3-difluoro-3-ethoxycarbonyl-2-hydroxy-1-isopropyl)acetamide The product of Example 21.g. was coupled using a procedure similar to that described in Example 1.g., except a catalytic amount of 4-dimethylaminopyridine was added. The product was purified by chromatography, eluting with dichloromethane:methanol (97:3), to afford the ester; TLC: R$_f$=0.17, chloroform:methanol (40:1, double elution); MS: m/z=621(M+1).

i. 2-[3-Benzyloxycarbonylamino-6-(2-chlorophenyl)-2-oxo-1,2-dihydro-1-pyridyl]-N-[3,3-difluoro-2-hydroxy-1-isopropyl-3-[N-[2-(4-methoxyphenyl)ethyl]carbamoyl]propyl]acetamide The product of Example 21.h. was coupled with 2-(4-methoxyphenyl)ethylamine using a procedure similar to that described in Example 1.h., except the reaction mixture was diluted with water; the pH was adjusted to 6–7 with 10% hydrochloric acid; and the crude amide was not further purified; TLC: R$_f$=0.20, chloroform:methanol (40:1); MS: m/z=726(M+1).

j. 2-(3-Amino-2-oxo-6-phenyl-1,2-dihydro-1-pyridyl )-N-[3,3-difluoro-2-hydroxy-1-isopropyl-3-[N-[2-(4-methoxyphenyl)ethyl]-carbamoyl]propyl]acetamide To a solution of the product of Example 21.i. (0.73 g) in methanol (10 mL), dry ice was added, causing bubbling. 10% (w/w) Palladium on carbon (0.15 g) was added, followed by ammonium formate (0.62 g). The reaction mixture was heated to reflux for 90 minutes. After cooling to room temperature, the mixture was filtered through diatomaceous earth. The plug was washed with hot ethanol. The filtrate was evaporated; and the residue was dissolved in dichloromethane, washed (water, brine), dried and evaporated to yield the product (0.43 g) which was not further purified; TLC: R$_f$=0.35, chloroform:methanol (40:1); 300 MHz NMR: 8.45 (t,1), 7.74 (d,1), 7.37 (s,6), 7.11 (d,2), 6.84 (d,2), 6.57 (d,1), 6.04 (t,2), 5.24 (s,1), 4.53–4.47 (d,1), 4.33–4.10 (m,2), 3.73–3.63 (m,4), 3.37–3.23 (m,1), 3.17–3.03 (m,1), 2.72–2.60 (m,2), 1.84–1.63 (m,1), 0.862 (d,3), 0.787 (d,3); MS: m/z=557(M+1).

k. 2-(3-Benzyloxycarbonylamino-2-oxo-6-phenyl-1,2-dihydro-1-Pyridyl)-N-[3,3-difluoro-2-hydroxy-1-isopropyl-3-[N-[2-(4-methoxyphenyl)ethyl]carbamoyl]propyl]acetamide To a suspension of the product of Example 21.j. (0.42 g) in tetrahydrofuran (4 mL) was added sodium carbonate (0.18 g) and dimethylformamide (0.08 mL). This produced gas evolution. Benzyl chloroformate (0.185 mL) was added dropwise; this produced a thick suspension which would not stir even with the addition of more solvent (4 mL). A mechanical stirrer was then used. After stirring overnight, the reaction was quenched with 10% hydrochloric acid and extracted with ethyl acetate. The organic phase was washed (brine), dried and evaporated to give the crude product (0.53 g) which was purified by chromatography, eluting with dichloromethane:methanol (97:3), to afford the urethane (0.40 g); TLC: R$_f$=0.40, dichloromethane:methanol (95:5); 300 MHz NMR: 8.58 (s,1), 8.35 (t,1), 7.95 (d,1), 7.79 (d,1), 7.53–7.30 (m,10), 7.07 (d,2), 6.81 (d,2), 6.25 (d,1), 6.06 (d,1), 5.18 (s,1), 4.45 (q (AB), 2), 5.27–4.17 (m,1), 3.84–3.63 (m,4), 3.40–3.10 (m,2), 2.5 (t,2), 1.80–1.67 (m,1), 0.851 (d,3), 0.773 (d,3); MS: m/z=691(M+1).

l. 2-(3-Benzyloxycarbonylamino-2-oxo-6-phenyl-1,2-dihydro-1-pyridyl)-N-[3,3-difluoro-1-isopropyl-3-[N-[2-(4-methoxyphenyl)-ethyl]carbamoyl]-2-oxopropyl]acetamide The product of Example 21.k. was oxidized using a procedure similar to that described in Example 1.i. except no acid wash was done. Purification by chromatography, eluting with chloroform:methanol (50:1), afforded the ketone; TLC: $R_f$=0.36, chloroform:methanol (40:1); 300 MHz NMR: 9.17 (t,1), 8.56–8.43 (dd,2), 7.91 (d,1), 7.55–7.29 (m,10), 7.10 (d,2), 6.84 (d,2), 6.22 (d,1), 5.19 (s,1), 4.80 (q,1), 3.71 (s,3), 3.38–3.24 (m,2), 2.50 (t,2H), 2.32–2.18 (m,1), 0.842 (d,3), 0.732 (d,3); MS: m/z=689(M+1). It is noted that this ketone is also a Compound of the invention.

EXAMPLE 22

2(3Acetylamino-2-oxy-6-phenyl-1,2-dihydro-1-pyridyl)-N-[-3,3-difluoro-1-isopropyl-3-(N-phenethylcarbamoyl)-2-oxopropyl]-acetamide Using a procedure similar to that described in Example 1.i., except omitting the acid wash, 2-(3-acetylamino-2-oxo-6-phenyl-1,2-dihydro-1-pyridyl)-N-[3,3-difluoro-2-hydroxy-1-isopropyl-3-(N-phenethylcarbamoyl)propyl] acetamide was oxidized and purified by chromatography, eluting with chloroform:methanol (40:1), to afford the title compound; TLC: $R_f$=0.20, chloroform:methanol (40:1); 300 MHz NMR: 9.34 (s,1), 9.21 (t,1), 8.51 (d,1), 8.26 (d,1), 7.50–7.13 (m,10), 6.18 (d,1), 4.82 (q,1), 4.49 (s,2), 3.43–3.29 (m,2), 2.76 (t,2), 2.21–2.13 (m,1), 2.13 (s,3), 0.852 (d,3), 0.7.44 (d,3); MS: m/z=567(M+1). Analysis for $C_{30}H_{32}F_2N_4O_5 \cdot 1.05\ H_2O$: Calculated: C, 61.54; H, 5.87; N, 9.57; Found: C, 61.53; h, 5.63; N, 9.59.

The starting alcohol was prepared as follows.

a. 2-[3-Benzyloxycarbonylamino-6-(2-chlorophenyl)-2-oxo-1,2-dihydro-1-pyridyl]-N-[3,3-difluoro-2-hydroxy-1-isopropyl-3-(N-phenethylcarbamoyl)propyl]acetamide 2-[3-Benzyloxycarbonylamino-6-(2-chlorophenyl)-2-oxo-1,2-dihydro-1-pyridyl]-N-[3,3-difluoro-2-hydroxy-1-isopropyl-3-(N-propylcarbamoyl)propyl]acetamide was treated with phenethylamine using a method similar to that described in Example 1.h. except that the reaction mixture was diluted with water, and the pH was adjusted to 6–7 with 10% hydrochloric acid; the mixture was evaporated; and the residue was partitioned between ethyl acetate and water. The organic phase was washed (10% hydrochloric acid, brine), dried and evaporated. Purification by trituration from ether afforded the amide; TLC: $R_f$=0.34, chloroform:methanol (40:1).

b. 2-(3-Amino-2-oxo-6-phenyl-1,2-dihydro-1-pyridyl)-N-[3,3-difluoro-2-hydroxy-1-isopropyl-3-(N-phenethylcarbamoyl)propyl]-acetamide Using a similar procedure to that described in Example 21.j., except the residue was dissolved in a mixture of chloroform and ethyl acetate instead of dichloromethane, the product of Example 22.a. was hydrogenolyzed to afford the 3-amino-6-phenyl derivative, which was used without further purification; TLC: $R_f$=0.25, chloroform:methanol (97:3) (2 elutions); MS: m/z=527(H+1).

c. 2-(3-Acetylamino-2-oxo-6-phenyl-1,2-dihydro-1-pyridyl)-N-[3,3-difluoro-2-hydroxy-1-isopropyl-3-(N-phenethylcarbamoyl)propyl]-acetamide Using a similar procedure to that described in Example 20.k., the product of Example 22.b. was acylated by treatment of a solution of the amine in tetrahydrofuran (4 mL) with triethylamine (0.061 mL), followed by acetyl chloride (0.031 mL), creating a suspension. When reaction was complete, the reaction mixture was diluted (ethyl acetate), washed (saturated sodium bicarbonate, brine), dried and evaporated. Purification by chromatography, eluting with dichloromethane:methanol (96:4), afforded the acetamido compound; TLC: $R_f$=0.14, chloroform:methanol (40:1); MS: m/z=569(H+1).

EXAMPLE 23

N[3,3-Difluoro-3-[N-(4-fluorobenzyl)carbamoyl]-1-isopropyl-2-oxopropyl]-2-(3-methoxycarbonylamino-2-oxo-6-phenyl-1,2-dihydro-1-pyridyl)acetamide Using a procedure similar to that described in Example 20.k., except omitting the use of dimethylformamide and omitting the acid wash, 2-(3-amino-2-oxo-6-phenyl-1,2-dihydro-1-pyridyl)-N-[3,3-difluoro-3-[N-(4-fluorobenzyl)carbamoyl]-1-isopropyl-2-oxopropyl]-acetamide was acylated using methyl chloroformate and the urethane purified by chromatography, eluting with dichloromethane:methanol (97:3), to afford the title compound; TLC: $R_f$=0.30, dichloromethane:methanol (95:5); 300 MHz NMR: 9.71 (t,1), 8.52 (d,1), 8.38 (s,1), 7.90 (d,1), 7.50–7.23 (m,7), 7.14 (t,2), 6.23 (d,1), 4.82 (t,1), 4.49 (s,2), 4.32 (d,2), 3.69 (s,3), 2.34–2.13 (m,1), 0.820 (d,3), 0.707 (d,3); MS: m/z=587(M+1). Analysis for $C_{29}H_{29}F_3N_4O_6$: Calculated: C, 59.38; H, 4.98; N, 9.55; Found: C, 59.53; H, 5.25; N, 9.18.

FORMULAE

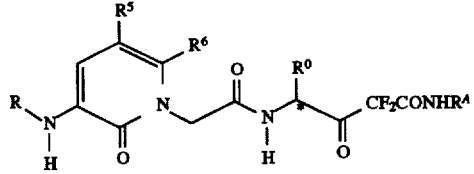

I

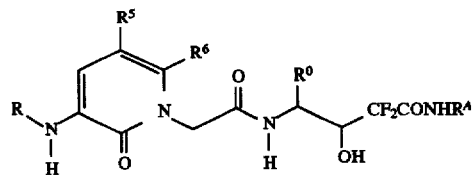

II

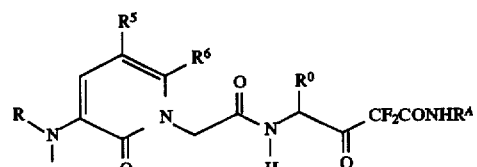

Vb

SCHEME I
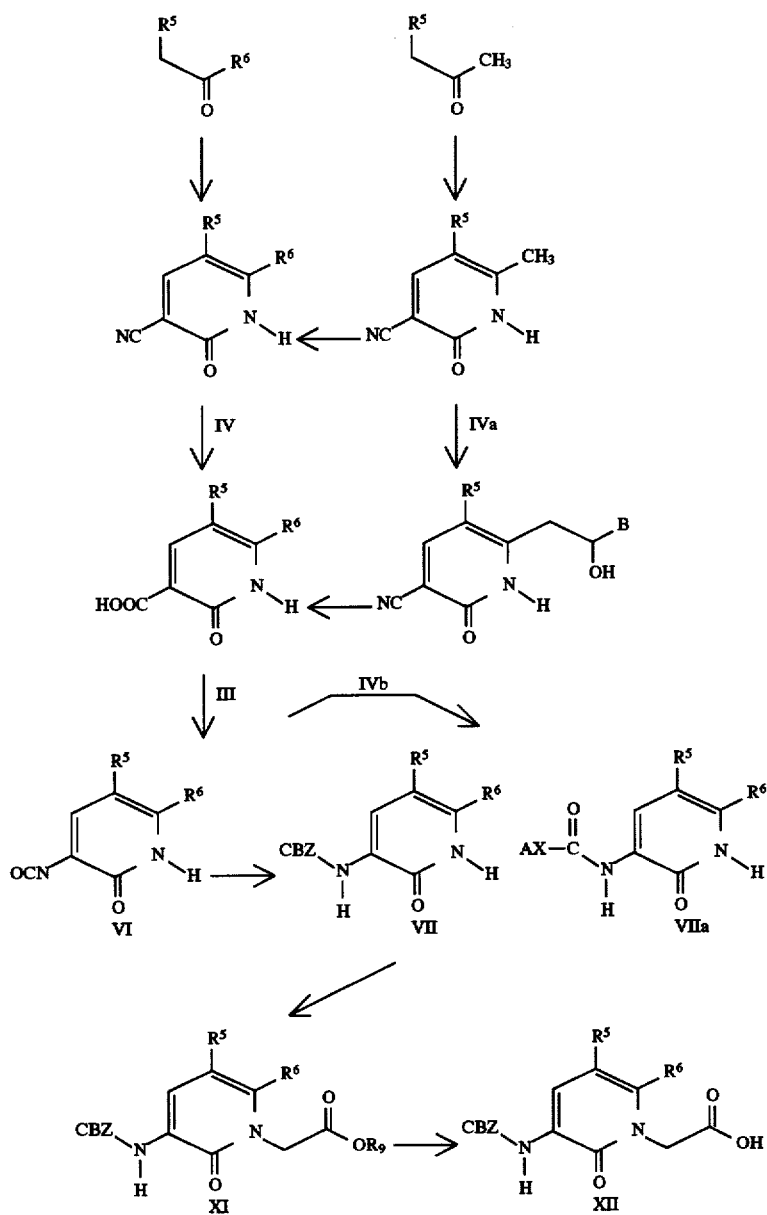
SCHEME Ia
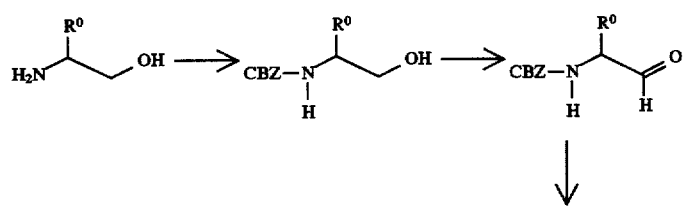

-continued
SCHEME Ia
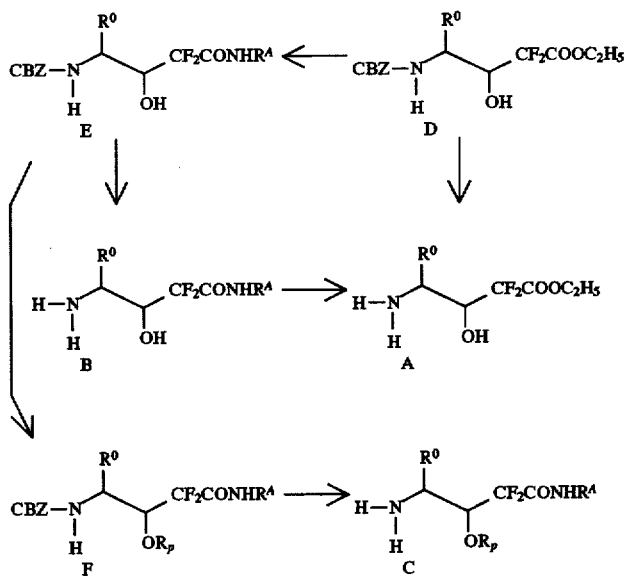
SCHEME II
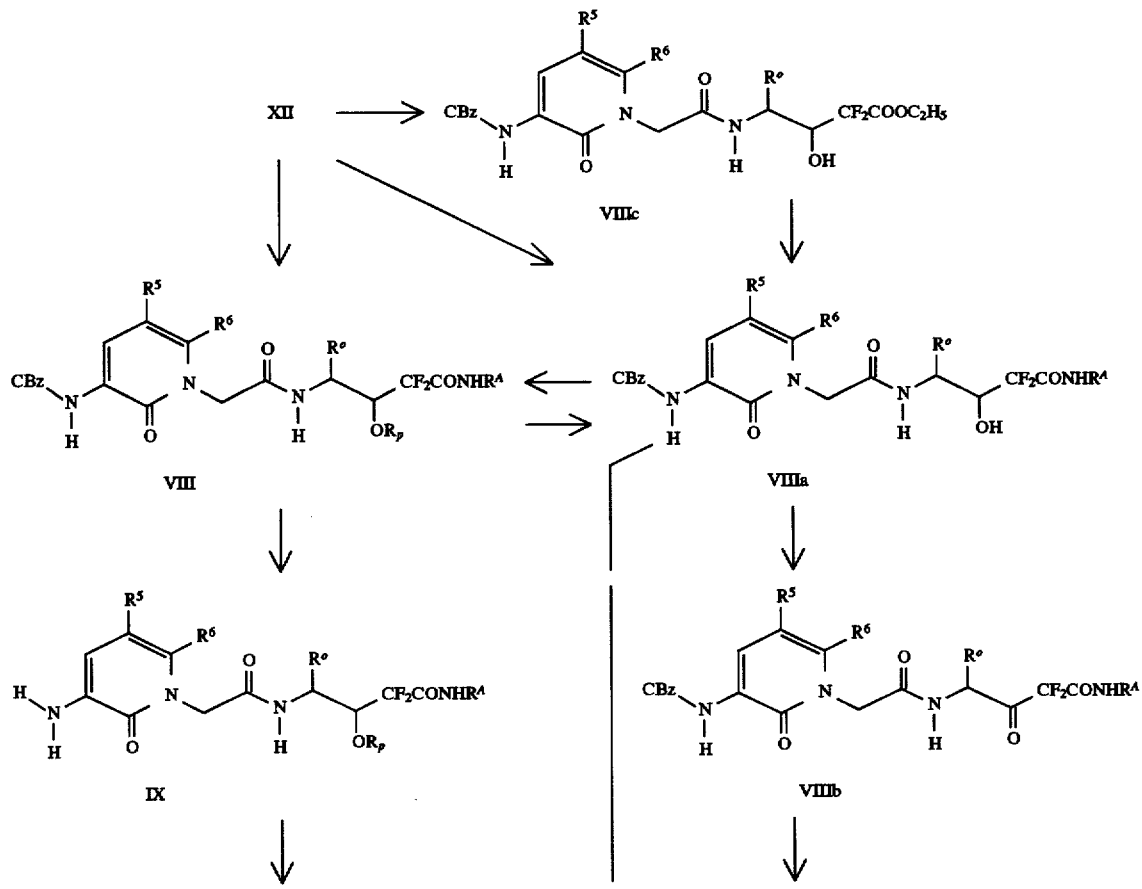

-continued
SCHEME II
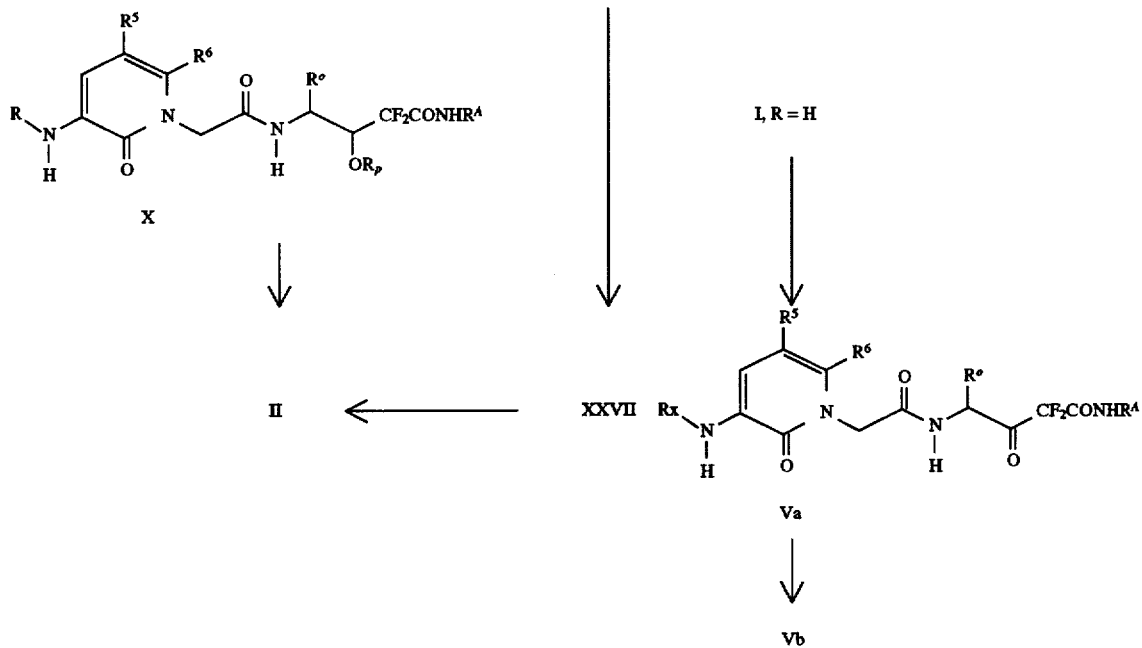
SCHEME III
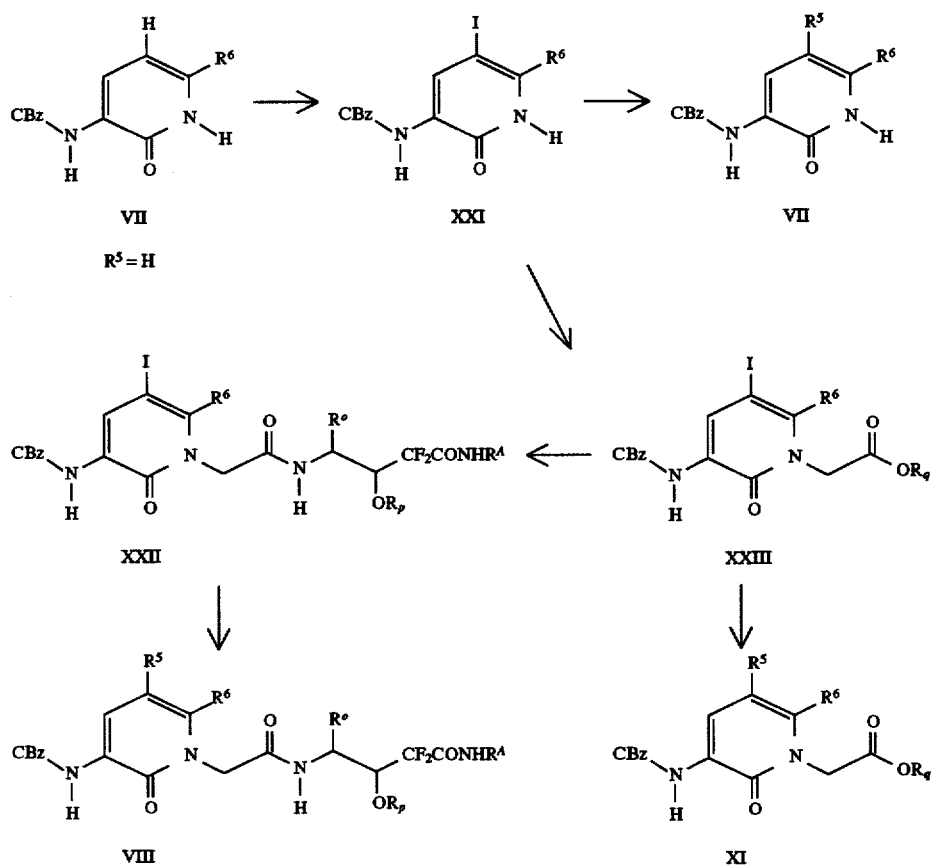

SCHEME IV
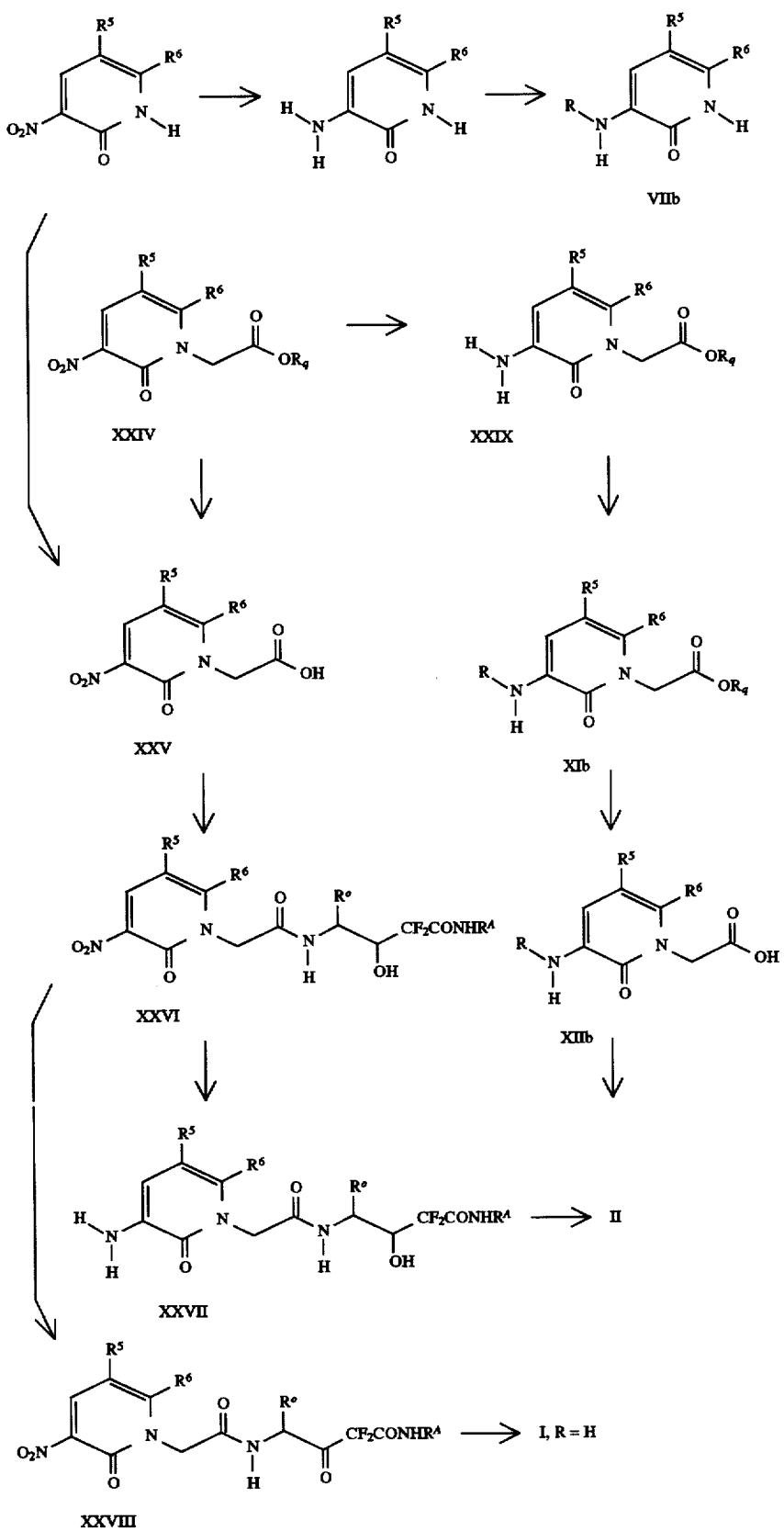

What is claimed is:

1. A compound of formula I

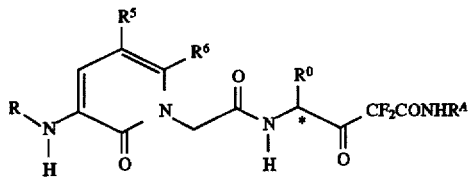

wherein:

$R^O$ is (1–5C)alkyl;

R is hydrogen; or

R is an acyl group of formula A.X.CO— in which A.X—, taken together, is trifluoromethyl; or R is an acyl group of formula A.X.CJ— in which J is oxygen;

X is a direct bond or oxy; and

A is (1–6C)alkyl, aryl, aryl(1–3C)alkyl, pyridyl or pyridyl(1–3C)-alkyl wherein an aryl or pyridyl moiety may bear one or more halogeno, nitro, methyl or trifluoromethyl groups and further wherein the group A may bear one or more substituents selected from a group consisting of hydroxy, lower alkoxy and lower acyloxy;

One of $R^5$ and $R^6$ is hydrogen or methyl and the other of $R^5$ and $R^6$ is a radical of formula B.Y— in which B is aryl, which aryl may bear one or more of the substituents defined for A;

Y is a direct bond, methylene, ethylene or trans-vinylene;

$R^A$ is (1–6C)alkyl, (3–6C)cycloalkyl, or (3–6C)cycloalkyl(1–3C)alkyl, wherein the group $R^A$ may bear one or more substituents selected from a group consisting of hydroxy, lower alkoxy, COORs, CONRtRu, $SO_2Rv$, $CONHSO_2Rv$, NRtRu, NRsCHO, NRsCORv, NRsCOORv, NRsCONRtRu, $NRsSO_2Rv$, $SO_2NRtRu$, $SO_2NRsCORv$, and $P(O)(ORv)_2$ in which Rs—Ru are independently hydrogen, benzyl or lower alkyl; and Rv is trifluoromethyl, (1–6C)alkyl, (3–6C)cycloalkyl or aryl; or for a compound of formula I which is acidic or basic, a pharmaceutically acceptable salt thereof.

2. A compound as claimed in claim 1 wherein $R^O$ is isopropyl; J is oxygen; X is a direct bond or oxy; A is methyl, ethyl, phenyl, benzyl, phenethyl, pyridyl, pyridylmethyl, or 2o(pyridyl)ethyl wherein the phenyl or pyridyl group may bear one or two halogeno or methyl groups and further wherein the group A may bear a substituent selected from hydroxy, methoxy, t-butoxy, acetoxy or pivaloyloxy.

3. A compound as claimed in claim 1 wherein R is hydrogen, trifluoroacetyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl or acetyl.

4. A compound as claimed in claim 2 wherein R is hydrogen, trifluoroacetyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl or acetyl.

5. A compound as claimed in any one of claims 1, 2, 3, or 4 in which $R^5$ is benzyl, the phenyl ring of which may bear a 3-fluoro, 4-fluoro, 4-trifluoromethyl, 3-acetoxy, 3-hydroxy, 3-pivaloyloxy, 4-hydroxy or 4-pivaloyloxy substituent, and $R^6$ is hydrogen.

6. A compound as claimed in any one of claims 1, 2, 3, or 4 in which $R^5$ is hydrogen, and $R^6$ is phenyl in which the phenyl may bear one or two halogeno, trifluoromethyl, methyl, hydroxy, methoxy or tert-butoxy substituents.

7. A compound as claimed in claim 6 wherein $R^6$ is phenyl or 4-fluorophenyl.

8. A compound as claimed in claim 1 which is 2-(3-amino-2-oxo-6-phenyl-1,2-dihydro-1-pyridyl)-N-[3,3-difluoro-1-isopropyl-2-oxo-3-(N-propylcarbamoyl)propyl] acetamide, or a pharmaceutically acceptable salt thereof.

9. A salt as claimed in claim 1 selected from (a) for an acidic compound of formula I, an alkalai metal salt, an alkaline earth metal salt, an aluminum salt, an ammonium salt, or a salt made from an organic base which affords a pharmaceutically acceptable cation; and (b) for a basic compound of formula I, an acid-addition salt made with an acid which provides a pharmaceutically acceptable anion.

10. A pharmaceutical composition comprising a pharmaceutically effective amount of a compound as defined in claim 1, or a pharmaceutically acceptable salt thereof, and a pharmaceutically acceptable diluent or carrier.

* * * * *